(12) United States Patent
Taylor

(10) Patent No.: US 6,492,103 B1
(45) Date of Patent: Dec. 10, 2002

(54) SYSTEM FOR ORGAN AND TISSUE PRESERVATION AND HYPOTHERMIC BLOOD SUBSTITUTION

(75) Inventor: Michael J. Taylor, Mt. Pleasant, SC (US)

(73) Assignee: Organ Recovery Systems, Inc., Des Plaines, IL (US)

( * ) Notice: Subject to any disclaimer, the term of this patent is extended or adjusted under 35 U.S.C. 154(b) by 0 days.

(21) Appl. No.: 09/628,311

(22) Filed: Jul. 28, 2000

Related U.S. Application Data
(60) Provisional application No. 60/179,153, filed on Jan. 31, 2000.

(51) Int. Cl.$^7$ ................................................ A01N 1/02
(52) U.S. Cl. ............................. 435/1.2; 435/2; 514/832
(58) Field of Search .............................. 514/832; 604/4; 435/1.1, 2, 1.2

(56) References Cited

U.S. PATENT DOCUMENTS

| | | | |
|---|---|---|---|
| 4,061,537 A | 12/1977 | Seiler et al. | |
| 4,238,482 A | 12/1980 | Peyman et al. | |
| 4,271,144 A | 6/1981 | Holly | |
| 4,403,038 A | 9/1983 | Asakura et al. | |
| 4,725,586 A | 2/1988 | Lindstrom et al. | |
| 4,740,594 A | 4/1988 | Mauzac et al. | |
| 4,798,824 A | 1/1989 | Belzer et al. | |
| 4,828,976 A | 5/1989 | Murphy | |
| 4,920,044 A | 4/1990 | Bretan, Jr. | |
| 4,923,442 A | 5/1990 | Segall et al. | |
| 4,927,806 A | 5/1990 | Kramer et al. | |
| 4,938,961 A | 7/1990 | Collins et al. | |
| 4,961,928 A | 10/1990 | Holme et al. | |
| 5,011,826 A | 4/1991 | Steudle et al. | |
| 5,082,831 A | 1/1992 | Leaf et al. | |
| 5,112,622 A | 5/1992 | Kopp | |
| 5,130,230 A | 7/1992 | Segall et al. | |
| 5,145,771 A | 9/1992 | Lemasters et al. | |
| 5,248,506 A | 9/1993 | Holme et al. | |
| 5,290,766 A | 3/1994 | Choong | |
| 5,306,711 A | 4/1994 | Andrews | |
| 5,328,821 A | 7/1994 | Fisher et al. | |
| 5,370,989 A | 12/1994 | Stern et al. | |
| 5,405,742 A | * 4/1995 | Taylor ........................... | 435/1 |
| 5,407,669 A | 4/1995 | Lindstrom et al. | |
| 5,498,427 A | 3/1996 | Menasche | |
| 5,514,536 A | * 5/1996 | Taylor ......................... | 435/1.2 |
| 5,552,267 A | 9/1996 | Stern et al. | |
| 5,554,497 A | 9/1996 | Raymond | |
| 5,574,019 A | 11/1996 | Segall et al. | |
| 5,599,659 A | 2/1997 | Brasile et al. | |
| 5,643,712 A | 7/1997 | Brasile | |
| 5,679,565 A | 10/1997 | Mullen et al. | |
| 5,693,462 A | 12/1997 | Raymond | |
| 5,699,793 A | 12/1997 | Brasile | |
| 5,702,880 A | 12/1997 | Segall et al. | |
| 5,702,881 A | 12/1997 | Brasile et al. | |
| 5,723,281 A | 3/1998 | Segall et al. | |
| 5,747,071 A | 5/1998 | Segall et al. | |
| 5,834,178 A | * 11/1998 | Churchill et al. ............ | 435/1.2 |
| 5,843,024 A | 12/1998 | Brasile | |

FOREIGN PATENT DOCUMENTS

| | | |
|---|---|---|
| WO | WO 86/00812 | 2/1986 |
| WO | WO 94/21116 | 9/1994 |
| WO | WO 96/12191 | 4/1996 |
| WO | WO 96/31779 | 10/1996 |
| WO | WO 97/22003 | 6/1997 |
| WO | WO 97/28449 | 8/1997 |

OTHER PUBLICATIONS

Bellamy et al., (1996), Crit. Care Med., vol. 24 No. 2, S24–S47.*

T. Horiuchi et al., "Machine Perfusion of Isolated Kidney at 37°C Using Pyridoxalated Hemoglobin–Polyoxyethylene (PHP) Solution, UW Solution and Its Combination," Bromat., Art. Cells & Immob. Biotech., 20(2–4), pp. 549–555 (1992).

T. Endoh et al., "Graft Conditioning of Liver in Non–Heart–Beating Donors by an Artificial Heart and Lung Machine in Situ," *Transplantation Proceedings*, vol. 28, No. 1, pp. 110–115 (1996).

R.S. Frank et al., "Ischemia With Intermittent Reperfusion Reduces Functional and Morphologic Damage Following Renal Ischemia in the Rat," *Ann. of Vasc. Surg.*, vol. 7, No. 2, pp. 150–155 (1993).

P. Julia et al., "Improvement of Postischemic Kidney Function by Reperfusion with a Specifically Developed Solution (BT01)," *Ann. of Vasc. Surg.*, vol. 9, pp. S–81–S–88 (1995).

C.E. Irazu et al., "Effect of Ischemia and 24 Hour Reperfusion on ATP Synthesis in the Rat Kidney," *Journal of Experimental Pathology*, vol. 4, No. 1, pp. 29–36 (1989).

A.O. Gaber et al., "Intermediate Normothermic Hemoperfusion of Rat Kidneys: Functional Aspects and a Study Into the Effect of Free Radical Scavengers," *Transplantation Proceedings*, vol. XX, No. 5, pp. 896–898 (1988).

P.L. Julia et al., "Studies of Controlled Reperfusion After Ischemia, XXI. Reperfusate Composition: Superiority of Blood Cardioplegia Over Crystalloid Cardioplegia in Limiting Reperfusion Damage—Importance of Endogenous Oxygen Free Radical Scavengers in Red Blood Cells," *J. Thorac. Cardiovasc. Surg.*, vol. 101, pp. 303–313 (1991).

B.L. Kasiske et al., "Mild Hypothermia Gives Better Functional Preservation Than Cold or Normothermic Perfusion of Rat Kidneys," *Transplantation Proceedings*, vol. 22, No. 2, pp. 472–473 (1990).

R.N. Dunn et al., "Is Normothermic Preservation an Alternative to Hypothermic Preservation?," *Organ Preservation Basic and Applied Aspects* (first page) (1981).

(List continued on next page.)

Primary Examiner—Jon P. Weber
(74) *Attorney, Agent, or Firm*—Oliff & Berridge, PLC

(57) ABSTRACT

A unified solution system for organ and/or tissue preservation and/or hypothermic blood substitution can be used to prepare multiple solutions for use in various stages of organ procurement, preservation and transplantation and bloodless surgery procedures.

30 Claims, 15 Drawing Sheets

OTHER PUBLICATIONS

A. Sundberg et al., "Urinary π–Class Glutathione Transferase as an Indicator of Tubular Damage in the Human Kidney," *Nephron*, vol. 67, pp. 308–316 (1994).

J.D. Hughes et al., "Normothermic Renal Artery Perfusion: A Comparison of Perfusates," *Ann. of Vasc. Surg.*, vol. 10, No. 2, pp. 123–130 (1996).

G. Kootstra et al., "The Asystolic, or Non–Heartbeating, Donor," *Transplantation*, vol. 63, No. 7, pp. 917–921 (1997).

J.G. Maessen et al., "The Beneficial Effect of Intermediate Normothermic Perfusion During Cold Storage of Ischemically Injured Kidneys," *Transplantation*, vol. 47, No. 3, pp. 409–414 (1989).

J.G. Maessen et al., "Intermediate Normothermic Perfusion During Cold Storage of Ischemically Injured Kidneys," *Transplantation Proceedings*, vol. 21, No. 1, pp. 1252–1253 (1989).

R.J. Ploeg et al., "Effect of Pharmacologic Agents on the Function of the Hypothermically Preserved Dog Kidney During Normothermic Reperfusion," *Surgery*, vol. 103, No. 6, pp. 676–682 (1988).

F.H. Daniels et al., "The Use of Hemoglobin Solutions in Kidney Perfusions," *CRC Critical Reviews in Biomedical Engineering*, vol. 9, Issue 4, pp. 315–344 (1984).

R. Grundmann et al., "Analysis of the Optimal Perfusion Pressure and Flow Rate of the Renal Vascular Resistance and Oxygen Consumption in the Hypothermic Perfused Kidney," *Surgery*, vol. 77, No. 3, pp. 451–461 (1976).

N.N. Kontuganov et al., "Preservation of the Isolated Kidney Under Normothermic Conditions by Perfusion with Perfluorotribuylamine Emulsion," translated from *Byulletin' Éksperimental'noi Biologii i Meditsiny*, vol. 95, No. 3, pp. 98–100 (1983).

\* cited by examiner

SYSTEM FOR ORGAN AND TISSUE PRESERVATION AND HYPOTHERMIC BLOOD SUBSTITUTION

This nonprovisional application claims the benefit of U.S. Provisional Application No. 60/179,153, filed Jan. 31, 2000.

BACKGROUND OF THE INVENTION

1. Field of Invention

This invention relates to organ preservation and hypothermic blood substitution. This invention particularly relates to compositions, processes and systems for organ and tissue preservation and/or hypothermic blood substitution.

2. Description of Related Art

Hypothermia is the bed rock of all useful methods of organ and tissue preservation, and has proven to be most effectively applied by controlling the extracellular environment of cells directly, and the intracellular environment indirectly, during cold exposure. Control of the extracellular environment of cells to optimise preservation is based upon different strategies that include either static cold storage (or flush preservation), or low temperature continuous perfusion. These different strategies call for different approaches to interventional control of the extracellular environment in order to optimize preservation, and hence different design elements for the solutions used to effect these strategies.

In principle, cold flush storage or preservation is based upon the premise that temperature reduction to near but not below the ice point (0° C.) precludes the need to support metabolism to any significant extent, and that the correct distribution of water and ions between the intracellular and extracellular compartments can be maintained by physical rather than metabolic means. During the period that metabolic pumps are inactivated, the driving force for transmembrane ion flux is the difference in ionic balance between intracellular and extracellular fluid. The driving force for water uptake (cell swelling) is the impermeant intracellular anions. Thus changes can be prevented or restricted by manipulating the extracellular environment to abolish chemical potential gradients. On this basis, a variety of flush, or organ washout, solutions have been devised and evaluated for cold storage. These solutions are often referred to as "intracellular" solutions due to their resemblance, in some respects, to intracellular fluid.

The principle design elements of the "intracellular" flush solutions has been to adjust the ionic balance (notably of the monovalent cations) and to raise the osmolality by including an impermeant solute to balance the intracellular osmotic pressure responsible for water uptake. However, the most important factor for the efficacy of cold flush solutions may be the prevention of cellular edema by inclusion of impermeant solutes since it has been established that ionic imbalances, especially potassium depletion, are readily and rapidly reversible.

Prior to 1988, the standard solution for clinical preservation of abdominal organs, principally the kidney, was Collins solution, which consists predominantly of potassium phosphate. magnesium sulfate and glucose. In recent years, however, this has been superseded either by a modified version called "EuroCollins" in which the magnesium sulfate is omitted, or more extensively by the University of Wisconsin solution (UW solution) in which much of the phosphate anion has been replaced with lactobionate, and in which glucose has been replaced with raffinose. These larger molecules provide better protection against adverse effects of cell swelling during hypothermic storage. The choice of solutions for heart preservation has been strongly influenced by the previous experience of cardiac surgeons with cardioplegic solutions in open-heart surgery. In this case the primary objective has been to produce rapid cessation of the heartbeat, and solutions were designed more with this in mind than with protection of the cells during preservation in mind. In particular, early studies suggested that the very high potassium levels (>100 mM) found in organ preservation solutions might be harmful to the heart. In fact, the solution most often used was St. Thomas's (Plegisol) with a potassium content of only 16 mM.

The choice of solution for cardioplegia and myocardial preservation remains controversial and widely varied. While UW solution has emerged as the industry standard for kidney, liver and pancreas, no such standard has been adopted for heart preservation. Moreover, the development of the variety of preservation solutions for organ storage has emphasized the need for careful optimization in relation to the specific characteristics of the tissue to be preserved.

Attention to biophysical properties of "intracellular" flush solutions, to restrict passive diffusional processes, has unquestionably led to the development of techniques that have provided the basis of clinical organ preservation during the past 30 years. Nevertheless, it is recognized that further optimization of cold flush solutions can be achieved by inclusion of biochemical and pharmacological components that will be effective in counteracting the deleterious effects of ischemia and reperfusion injury. To a limited extent this approach has been incorporated in the design of the University of Wisconsin organ preservation solution (UW solution marketed as "Viaspanrm"; DuPont) which has become the most widely used solution for cold flush preservation of kidneys, livers and pancreases. With due consideration for the effects of ischemia, hypoxia, hypothermia and reperfusion injury on cells, coupled with the proven efficacy of various existing organ preservation solutions, a general consensus of the most important characteristics in the design of hypothermic storage solutions has emerged. These include: minimizing of hypothermically induced cell swelling; preventing expansion of the interstitial space (especially important during perfusion); restricting ionic imbalances; preventing intracellular acidosis; preventing injury from free radicals; and providing substrates for regeneration of high energy phosphate compounds during reperfusion.

In continuous hypothermic perfusion preservation, the desirable properties of hypothermic solutions listed above are also applicable to controlling the extracellular environment by way of continuous perfusion techniques. In contrast to static cold storage, continuous perfusion is usually controlled at around 10° C. and is based upon a different principle: it is generally assumed that a moderate degree of cooling will reduce metabolic needs but that continuous perfusion is required to support the suppressed metabolism and remove catabolic products. Because it is assumed that sufficient metabolic activity remains to actively regulate a near-normal cell volume and ionic gradients, the perfusates are generally acellular, isotonic, well oxygenated solutions having a composition that more closely resembles plasma than intracellular fluid. Such perfusates are therefore designated as "extracellular" solutions, and are perfused through the vascular bed of an organ at a pressure sufficient to achieve uniform tissue distribution (typically 40–60 mm Hg). To balance this applied hydrostatic pressure and prevent interstitial edema, oncotic agents such as albumin or synthetic macromolecular colloids are incorporated into the perfusates. Substrate support of the remaining metabolism at ~10° C. is also an important consideration and it has been shown in several organs that high energy adenine nucleotides can be synthesized during hypothermic perfusion preservation.

In addition to the principal objective of supporting metabolism, continuous perfusion also provides other advantages over flush preservation. These include the wash out of accumulated lactate and protons, thereby removing the metabolic block on glycolysis; this is thought to be especially beneficial for organs that have suffered prior warm ischemia. Perfusion also facilitates the removal of erythrocytes from the microcirculation and helps to maintain vascular patency during prolonged storage. Continuous perfusion has been shown to provide the best means of achieving prolonged hypothermic preservation (e.g., 3–7 days for kidneys), but concerns for damage to the vascular endothelium during prolonged perfusion may be a limiting factor.

Although it has been experimentally verified that cell metabolism continues at temperatures as low as 10° C., and that adenine nucleotides can be resynthesized during hypothermic preservation if appropriate substrates are provided, it is considered unlikely that this level of metabolism can prevent transmembrane ion and water movements: this is due principally to the temperature sensitivity of the active pumps. Hence, some advocates of continuous perfusion have modified the perfusate accordingly by increasing both the $K^+$ concentration and the osmolality. Similarly, modification of cold flush solutions can be considered to circumvent some of the identified limitations of that approach. For example, the lack of support of metabolism during ice-storage can be addressed by raising the temperature of storage, by incorporating biochemical substrates and raising the oxygen tension to promote adenine nucleotide repletion. Also, the use of pharmacological agents, such as inhibitors of 5'-nucleotidase (e.g., allopurinol) has been advocated as a means of averting adenine nucleotide depletion.

With respect to specific cell requirements as a function of temperature, it is not necessary to consider incorporating specific oxygen-carrying molecules at temperatures below ~10° C. since at such low temperatures it is well established that metabolic activity is sufficiently depressed that the $O_2$ demand can be satisfied by dissolved $O_2$ in the aqueous solution without the need for hemoglobin or synthetic $O_2$-carrying molecules.

Optimum control of the intracellular and extracellular environment of cells during hypothermia depends upon the interaction of a variety of factors that include temperature, oxygen tension, acidity, osmotic pressure and chemical composition of the perfusion fluid or wash-out solution.

It is now recognized that the successive phases of the transplantation procedure involving organ procurement, storage, transportation, reimplantation and reperfusion may impose different requirements for optimum preservation at the different stages. This is illustrated by evidence that heart preservation with the "intracellular" solution, EuroCollins, was enhanced when the heart was initially arrested and subsequently flushed prior to reperfusion, with an "extracellular" cardioplegic solution. Therefore, any single formulation of preservation solution is unlikely to provide optimum protection during all the processing stages of a transplantation procedure, or the interventional stages of complex surgeries.

Interest in general or universal tissue preservation techniques is exemplified by the need for methods of protecting multiple vital organs, and even the whole body, for applications in modern day surgery. Multiple organ harvesting for transplantation can be optimized by hypothermic perfusion of the whole cadaver, or donor organ blocks comprising several organs, to minimize warm ischemic injury. The ultimate challenge is perhaps protection of the entire body against the effects of global ischemia during periods of circulatory and/or cardiac arrest for "bloodless" surgery.

Surgeons have developed skills that allow very complex, corrective and life-saving operations to be performed, notably on the heart and brain. Many of these complicated time-consuming procedures have the inherent need for temporary cessation of blood flow and demand protection of the patient against the deleterious effects of ischemia and anoxia. Although hypothermia is routinely used as an adjunctive protective modality for surgical procedures that require a period of cardiac arrest, there are restrictive time constraints (<1 hour at temperatures usually not lower than 18° C.) upon the safe interval of cold ischemia if neurological sequelae are to be avoided. It is well recognized that the window of opportunity for safe surgical intervention could be extended by using greater degrees of hypothermic metabolic suppression, but this becomes unacceptably dangerous due principally to the effects of profound hypothermia on the blood, leading to coagulopathies and irreversible microvascular blockage.

U.S. Pat. Nos. 5,643,712, 5,699,793, 5,843,024 to Brasile and U.S. Pat. Nos. 5,599,659, 5,702,881 to Brasile et al., each of which is incorporated herein by reference in its entirety, describe separate resuscitation and preservation solutions for tissues and organs. The Brasile patents disclose methods in which some embodiments of the compositions of this invention can be applied. Also, the Brasile patents disclose compositions that may be used in methods and kits of this invention.

The present inventor has explored experimental approaches employing a technique of asanguineous blood substitution using acellular synthetic solutions designed to protect the heart, brain and visceral organs during several hours of bloodless perfusion. The concept of using ultraprofound hypothermia (<10° C.) and complete blood replacement is appealing for several reasons and is based upon a variety of factors. First, deeper hypothermia can provide more effective suppression of metabolism, thereby extending the tolerance to ischemia and minimizing the demand for oxygen to levels that can be adequately supplied in a cold aqueous solution without the need of special oxygen-carrying molecules. Second, complete exsanguination ameliorates a complication associated with increased viscosity, coagulopathies, and erythrocyte clumping of cooled blood. Third, vascular purging can remove harmful catabolic products and formed elements that might participate in the ischemia and reperfusion injury cascades. A fourth advantage is that total exsanguination provides the opportunity to control the vascular and extracellular compartments directly with fluids designed to be protective under the conditions of ultraprofound hypothermia. For example, solutes can be added to maintain ionic and osmotic balance at the cellular and tissue levels; biochemical and pharmacological additives can help sustain tissue integrity in a variety of ways including efficient vascular flushing, membrane stabilization, free-radical scavenging and providing substrates for the regeneration of high-energy compounds during rewarming and reperfusion. In essence, these are the principles that are embodied, to a greater or lesser extent, in the design of various solutions used for ex vivo organ preservation. In this invention, similar principles have been adopted in the design of new hypothermic blood substitutes.

The working hypothesis that was used to evaluate this approach has been that an acellular solution can be designed to act as a universal tissue preservation solution during several hours of hypothermic whole-body washout involving cardiac arrest, with or without circulatory arrest. Under this hypothesis, Taylor et al. have formulated and evaluated two solutions designated Hypothermosol™-purge (HTIS-P) and Hypothermosol™-maintenance (HTS-M) that fulfill separate requirements during the asanguineous procedure. Some aspects of these solutions are described in U.S. Pat. Nos. 5,405,742 and 5,514,536 to Taylor, both of which are incorporated herein by reference in their entireties. The Taylor patents disclose methods in which some embodiments of the compositions of this invention can be applied. Also, the Taylor patents disclose compositions that may be used in methods and kits of this invention.

The principal solution (HTS-M) is a hyperkalemic "intracellular" solution specifically designed to "maintain" cellular integrity during the hypothermic interval at the lowest temperature. The second solution is designed to interface between the blood and the HTS-M maintenance solution during both cooling and warming. This companion solution is, therefore, an "extracellular" flush solution designed to aid in purging the circulation of blood during cooling since the removal of erythrocytes from the microvasculature is an important objective during ultraprofound hypothermia. The "purge" solution is also designed to flush the system (vasculature and CPB circuit) of the hyperkalemic HTS-M solution during warming and possibly help to flush-out accumulated toxins and metabolic byproducts that might promote oxidative stress and free radical injury upon reperfusion.

Based upon the principles that have emerged from isolated organ preservation studies, an attempt was made to incorporate some of the important characteristics in the formulation of the Hypothermosol™ solutions and, wherever possible, components that might fulfill multiple roles were selected. This strategy maximizes the intrinsic qualities of the solutions that, by design as universal tissue preservation solutions, would inevitably be a hybrid of other hypothermic perfusates and storage media.

The composition of the Hypothermosol™ blood substitutes and the rationale for their formulation are discussed in U.S. Pat. Nos. 5,405,742 and 5,514,536 to Taylor, both of which are incorporated herein by reference in their entireties. These solutions have been shown to protect the brain, heart and visceral organs during 3.5 hours of cardiac arrest and global ischemia in an asanguineous canine model during controlled profound hypothermia at <10° C. Successful application of this technique to man would provide more than a 3-fold extension of the current limits of <1 hour for "safe" arrest without a high risk of neurological complications. This novel approach to bloodless surgery would significantly broaden the window of opportunity for surgical intervention in a variety of currently inoperable cases, principally in the areas of cardiovascular surgery, neurosurgery and emergency trauma surgery.

More recently, the Hypothermosol™-maintenance solution has been used for in vitro hypothermic preservation of a variety of tissues and organs including isolated hearts, fetal spinal cord and engineered skin.

SUMMARY OF THE INVENTION

The present invention is based upon the concept of a unified solution system for preparing multiple solutions designed and optimized for the various stages of organ or tissue procurement-preservation-transplantation and/or bloodless surgery procedures.

While the known systems, including those taught in the Brasile and Taylor patents discussed above, have required completely different compositions for different stages of organ procurement, preservation and transplantation procedures, the present invention provides one or two (or optionally more) base compositions and a number of different additives that can be added to one or more of the base compositions to produce specific compositions useful for specific stages in organ or tissue procurement, preservation and transplantation and/or bloodless surgery procedures. In embodiments, the base and additives can be stored in separate containers in a single package or kit. Specific improved base compositions are also provided.

DETAILED DESCRIPTION OF PREFERRED EMBODIMENTS

Figure 1:
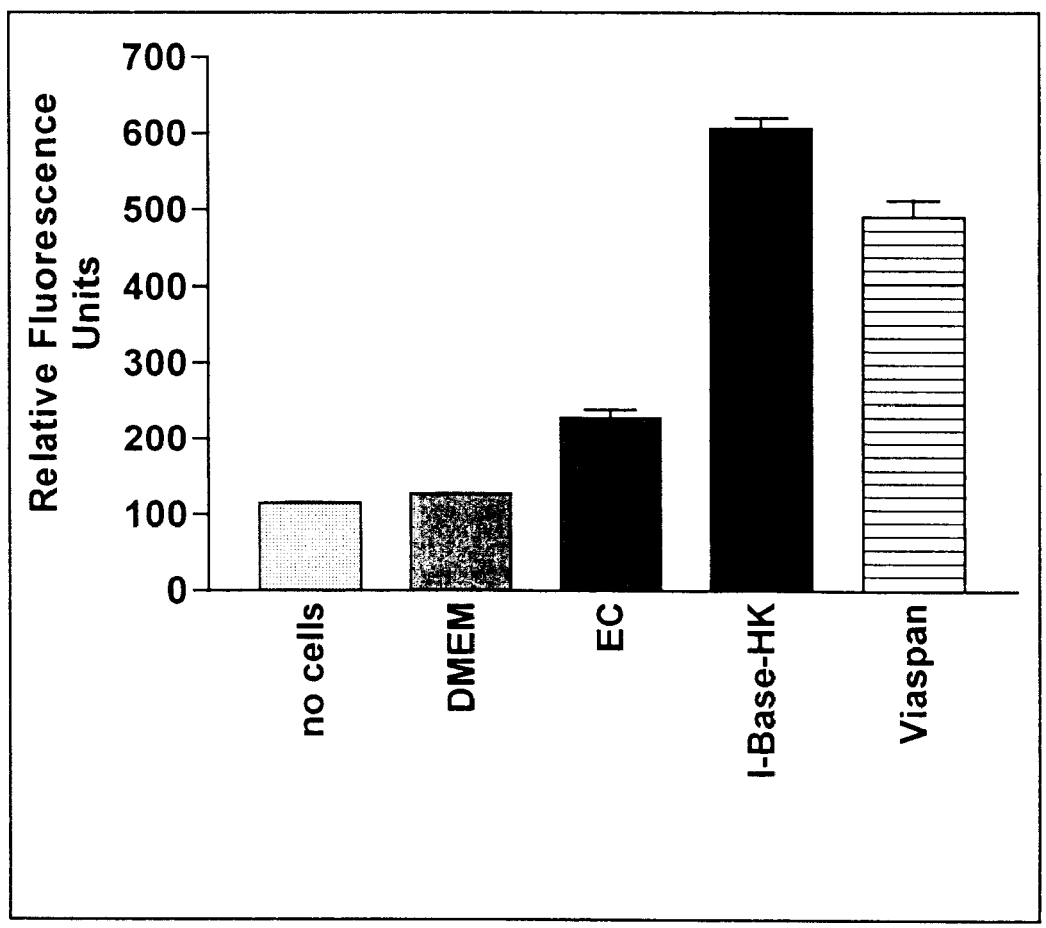
FIG. 1 shows the viability index for MDCK cells after a storage interval.
Figure 2:
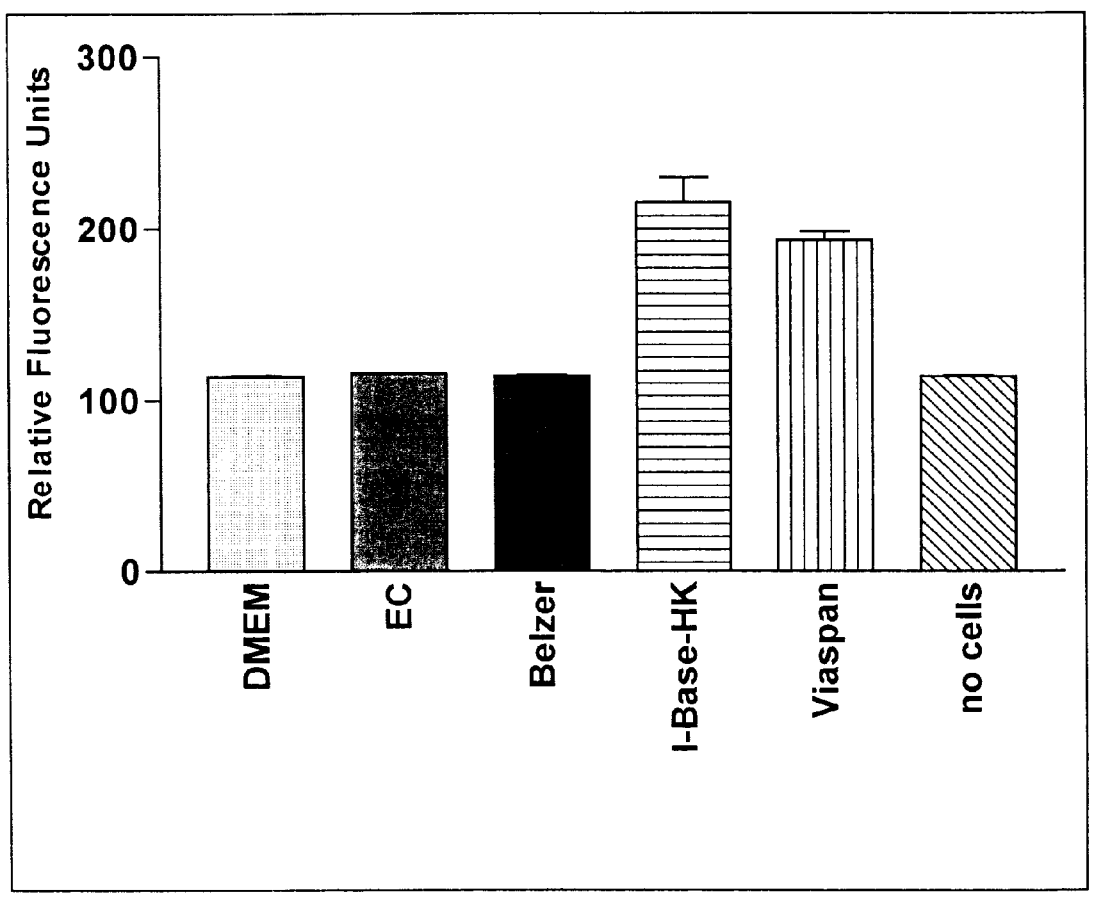
FIG. 2 shows the comparative viability of A10 cells after a one-day storage interval.
Figure 3:
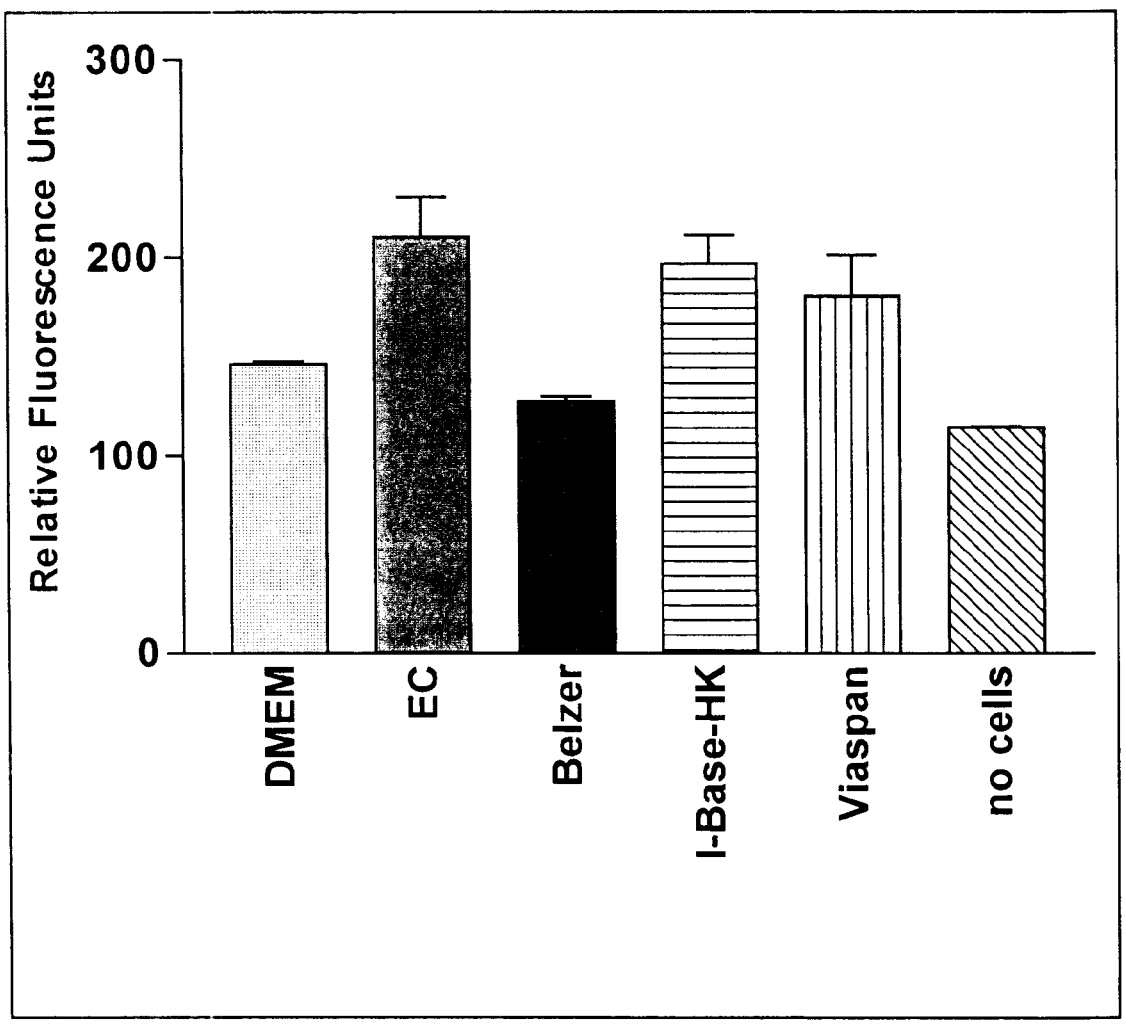
FIG. 3 shows the comparative viability of CPAE cells after a one-day storage interval.

This invention provides a unified solution system for preparing multiple solutions designed and optimized for various stages of organ and/or tissue procurement, preservation and transplantation and/or bloodless surgery procedures.

In preferred embodiments, the present invention provides one or two base compositions and a number of different additives that can be added to the base composition(s) to produce specific compositions useful for specific stages in the organ procurement, preservation and transplantation and/or bloodless surgery procedures. In embodiments, the base and additives can be stored in separate containers in a single package or kit.

A base formulation includes a design which takes into account the biophysical and minimal biochemical components that can be standardized for all or a desired subset of applications. This base unified solution can then be used as a vehicle for a range of additive "cocktails" to derive a system of solutions optimized for different needs.

In embodiments of the unified solution system series of solutions, solutions for warm ischemic time-organ preservation can include, for example, a hypothermic flush/purging solution, a hypothermic perfusate/maintenance solution, a "Normothermic" perfusate/rescue solution and/or a pre-reimplantation flush/rinse solution.

Exemplary embodiments of the unified solution system series can include, for example, the following base solutions:

Unified solution system Intracellular Base Solution: minimum requirements for cold storage including cryopreservation solutions. An exemplary formulation of such a solution as a preferred embodiment is given in Table 2.

Unified solution system Extracellular Base Solution: plasma-like electrolytes as base for oxygen carrying molecules and other substrates necessary for optimized "normothermic" perfusion.

Exemplary embodiments of the unified solution system series can include, for example, the following base plus additive solutions:

embodiment, the intracellular base is preferably concentrated to a 3x to 4x strength in comparison to its use alone and with most other additives. This facilitates its combination with additive cryoprotective compounds.

Examples of some illustration additives that can be utilized in accordance with this invention are listed in Table 3, although many other additives can be used.

Exemplary solutions for a clinical organ preservation program are summarized in Table 1.

TABLE 1

Solution Design Strategy for Clinical Organ Preservation Program

| Application Phase | Temperature Range | Base Solution Type | Additives |
|---|---|---|---|
| Organ Preparation in situ/ex vivo purge | 10–37° C. | Extracellular | Purging cocktail |
| Organ Maintenance cold flush | 0–4° C. | Intracellular (High K) | Protection/Maintenance cocktail |
| Organ Maintenance cold machine perfusion or cardiopulmonary bypass | 5–15° C. | Intracellular (High K or Na) | Protection/Maintenance cocktail |
| Organ Rescue warm machine perfusion | 30-37° C. | Extracellular | Rescue cocktail |
| Organ Pre-reimplantation ex vivo rinse | 30-37° C. | Extracellular | Plasma-like |

TABLE 2

Formulaton of unified solution system Intracellular Base (High Potassium)

| | | | | | | | |
|---|---|---|---|---|---|---|---|
| $Na^+$ | 62.5 mM | $Cl^-$ | 30.1 mM | HEPES | 35 mM | Dextran - 40 | 6% |
| $K^+$ | 70 mM | $H_2PO_4$ | 2.5 mM | Lactobionate | 30 mM | Glucose | 5 mM |
| $Ca^{2+}$ | 0.05 mM | $HCO_3^-$ | 5 mM | Gluconate | 70 mM | Adenosine | 2 mM |
| $Mg^{2+}$ | 15 mM | | | Sucrose | 15 mM | reduced Glutathione | 3 mM |
| | | | | Mannitol | 25 mM | | |

Purge=Extracellular Base plus purge additive ("cocktail") designed principally to purge the vasculature of blood in preparation for preservation.

Maintenance=Intracellular Base plus cytoprotection additive ("cocktail") designed to protect and maintain cellular stability during cold storage. Ideally, this will apply to both static cold storage and cold machine perfusion.

Rescue=Extracellular Base plus rescue additive ("cocktail") for near nomothermic perfusion.

Rinse=Extracellular Base plus rinse additive ("cocktail") designed to flush out unwanted preservation molecules prior to reimplantation. This may fulfill a different role from the Purge solution designed to remove erythrocytes and other blood components prior to the preservation phase.

Cryo=Concentrated Intracellular Base plus permeating or non-permeating cryoprotective additives for sub-zero preservation of cells and tissues. For the Cryo

TABLE 3

Exemplary Biochemical and Pharmacological Additives for Preservation Media

| Classification | Examples |
|---|---|
| Anti-platelet aggregation/vasoactive agents | Prostacyclin, Prostaglandin E-1 (PGE1), $Mg^{2+}$ |
| Calmodulin inhibitors | Chlorpromazine (CPZ), trifluoperazine |
| Calcium Channel Blockers | Nicardipine, nifedipine, verapamil, CPZ |
| Protease and phospholipase inhibitors | CPZ, verapamil, calpain antagonists |
| Anti-oxidants/free radical scavengers | Glutathione, catalase, super oxide dismutase (SOD), allopurinol, dimethylthiourea, vitamin-E (or Trolox), magnesium ascorbyl phosphate, Lazaroids |
| Anti-apoptotic agents | cycloheximide |
| Iron chelators | Desferroxamine |
| Membrane Stabilizers | CPZ, Dexamethosone, trehalose |
| "Cytoprotective" agents | PGE1, glycine |

TABLE 3-continued

Exemplary Biochemical and Pharmacological
Additives for Preservation Media

| Classification | Examples |
| --- | --- |
| Metabolic Substrates: | |
| Sugars | glucose, fructose, ribose |
| Nucleotide precursors (HEP enhancers) | Adenine, Adenosine, Fructose diphosophate, Glyceraldehyde-3-phosphate |
| Oxygen-carriers | Perfluorocarbons, PEG-hemoglobin |
| Trophic Factors | Growth factors, nucleic acid derivatives, ribonucleotides, glycosaminoglycans |
| Cryoprotective Additives (CPA) | Dimethylsulfoxide (DMSO), glycerol, propanediol, ethylene glycol, butanediol, polyvinylpyrrolidone (PVP), hydroxyethyl starch (HES), polyethylene glycol (PEG) |

A substantial number of improvements in the combinations of components and their respective concentrations have been incorporated in the design of the compositions and systems of this invention over that of the known art, including Hypothermosol™.

Based upon the principles that have emerged from isolated organ preservation studies over the past few decades, a list of desirable properties of a hypothermic blood substitute solution has emerged, as discussed above. As outlined above, the strategic designs of solutions used for organ preservation have differed depending upon their ultimate use, either as flush solutions for static storage of the organ, or as perfusates for continuous, or intermittent, perfusion of the organ. As a unique approach, the unified solution system of this invention has been formulated with a view to developing universal solutions that may be used for both hypothermic static storage of tissues and organs, and also for machine perfusion preservation. An attempt has been made to combine the main characteristics of effective hypothermic solutions in the formulation of the base solution, and wherever possible, components that might fulfill multiple roles have been selected. For example, an extracellular base solution in accordance with this invention may be combined with various different additives to form purging solutions, organ rescue solutions, pre-implantation rinses and the like. This strategy maximizes the intrinsic qualities of the solution that, by design as a universal tissue preservation solution, would inevitably be an improved hybrid of other hypothermic perfusates and storage media.

Salient design features for desirable base solutions are described below. Reference may also be made to U.S. Pat. No. 5,405,742, which is incorporated by reference herein in its entirety, for such features.

A fundamental biophysical property is to provide the optimum concentration of ions and colloids to maintain ionic and osmotic balance within the organ, or body tissues during hypothermia. In particular, one or more effective impermeant anions is or are included to partially replace chloride in the extracellular space and prevent osmotic cell swelling (i.e., to balance the fixed ions inside cells that are responsible for the oncotic pressure leading to osmotic cell swelling and eventual lysis during ischemia and hypothermia). A number of anions including citrate, glycerophosphate, gluconate and lactobionate, or the anionic forms of aminosulphonic acids, such as HEPES (N-2 (hydroxyethyl-piperazine)N-2-ethanesulfonic acid), TES (N-tris(hydroxymethyl)methyl-2-aminoethane sulfonic acid), MOPS (3-(n-morpholino)propanesulfonic acid), TAPSO (3-3 N-tris(hydroxymethyl) methylaminohydroxypropane sulfonic acid) and DIPSO (2-3 N-bis(hydroxyethyl)amino 2-hydroxypropanesulfonic acid) could be suitable candidates. Lactobionate (FW=358) was used exclusively as the principal impermeant in many solutions developed in recent years; these include, for example, Viaspan™, Hypothermosol, Celsior, Cardiosol and Churchill's solution. Lactobionate is also known to be a strong chelator of calcium and iron and, may therefore contribute to minimizing cell injury due to calcium influx and free radical formation.

However, for organ perfusion, Belzer and Southard (*Organ Preservation,* Annual Review of Medicine 1994; 46:235–247) teach against using lactobionate in a perfusion solution, especially for kidneys. Moreover, Belzer and Southard have explained the importance of lactobionate as a crucial component of UW solution that could not be successfully replaced with a similar anion, such as gluconate. Belzer and Southard therefore teach separate and exclusive roles for lactobionate and gluconate in organ preservation solutions using either the cold static storage, or perfusion approaches, respectively. Furthermore, Belzer teaches away from a combined approach that attempts to incorporate the best of simple flush storage and continuous perfusion because of "spectacularly poor results" (see "*Organ Preservation: Basic and Applied Aspects*", Ed D. E. Pegg et al., 1982, p339).

The osmotic components of this invention can be supplemented by the inclusion of sucrose and mannitol, the latter of which also possesses properties as a hydroxyl radical scavenger and reduces vascular resistance by inducing a prostaglandin-mediated vasodilation which may be of additional benefit.

A macromolecular oncotic agent is an important component of a blood substitute perfusate to help maintain oncotic pressure equivalent to that of blood plasma. Any oncotic agent that is sufficiently large to prevent or restrict its escape from the circulation by traversing the fenestration of the capillary bed may be considered. Examples of acceptable colloidal osmotic agents include blood plasma; expanders, such as human serum albumin; hetastarch or hydroxyethyl starch (HES), an artificial colloid derived from a waxy starch and composed almost entirely of amylopectin with hydroxyethyl ether groups introduced into the alpha (1–4) linked glucose units, a gelatin polypeptide; polyethylene glycol; and polysaccharide polymers of D-glucose, such as the dextrans. A preferred oncotic agent is dextran-40 (average mol wt=40,000 daltons) to balance the hydrostatic pressure of perfusion and help prevent interstitial edema. It has long been known that dextran can improve the efficiency of the removal of erythrocytes from the microvasculature of cooled organs by inhibiting red cell clumping and by increasing intravascular osmotic pressure and reducing vascular resistance. Dextran is widely used clinically as a plasma expander and is readily and rapidly excreted by the kidneys. Moreover, there is ample recent evidence that dextran-40 is an effective and well tolerated colloid in modern cold storage solutions for organ preservation.

Retention of the colloid in the vascular space is an important consideration for achieving optimal oncotic support and, in the context of isolated organ perfusion over several days, other colloids might be preferred to dextran-40. However, for whole-body perfusion for the order of 3 hours, the relative permeability of different colloids may be of less importance than other qualities, and non-antigenic clinical grade dextran-40 is preferred for the reasons outlined above. Any dextran that should permeate into the interstitial space during the hypothermic procedure will also be readily eluted upon return to physiological conditions.

Another possible advantage of the use of dextran is that the viscosity of the blood substitute will not be as high as with some other colloids, such as HES. This is also an important consideration for Theological aspects of whole-body, or even just cerebral perfusion. While the preferred embodiment described herein relates to kidney preservation in the first instance, the universal design strategy of the unified solution system is intended for widespread hypothermic applications including total body washout.

Ionic balance, notably the $Na^+/K^+$ and $Ca^{2+}/Mg^{2+}$ ratios, is preferably adjusted to restrict passive diffusional exchange at low temperatures when ionic pumps are inactivated. In the preferred high potassium embodiment of the unified solution described above, the concentration of monovalent cations $Na^+$ and $K^+$ are approximately equimolar to restrict their passive transmembrane exchange. In an alternative low potassium embodiment of the unified solution system, the balance of Na/K is changed to 125/25 in consideration of concerns for a toxic effect of high concentrations of $K^+$ in the heart. The concentration is kept sufficiently high to retain a cardioplegic effect of the solution. In the area of cardioplegia and myocardial preservation, there is good evidence for improved survival using elevated concentrations of magnesium and very low, but not zero, calcium to avoid the putative calcium paradox. Some glucose is included in these hypothermic solutions as a substrate, but the concentration is low to prevent exogenous overload during hypothermia. This can potentiate lactate production and intracellular acidosis by anaerobic glycolysis.

Acidosis is a particular hazard during hypothermia and attention has been given to the inclusion of a pH buffer that will be effective under non-physiological conditions that prevail at low temperatures. HEPES is preferred as one of the most widely used biocompatible aminosulphonic acid buffers, which have been shown to possess superior buffering capacity at low temperatures, and have been included as a major component of other hypothermic tissue preservation media. Synthetic zwitterionic buffers, such as HEPES, also contribute to osmotic support in the extracellular compartment by virtue of their molecular size (HEPES=238 daltons). Adenosine is a multi-faceted molecule and may be included in the hypothermic blood substitutes not only as a substrate for the regeneration of ATP during rewarming, but also as a vasoactive component to facilitate efficient vascular flushing by vasodilatation. Glutathione may be included as a cellular anti-oxidant and hydroxyl radical scavenger, as well as a co-factor for glutathione peroxidase which enables metabolism of lipid peroxides and hydrogen peroxide.

Perfusion apparatus and methods in which embodiments of this invention can be utilized are described in copending U.S. Pat. application Ser. No. 09/162,128, which is hereby incorporated by reference herein in its entirety.

Exemplary aqueous formulations of both intracellular and extracellular base solutions are illustrated below. The formulations can contain substantially about the amounts listed.

Exemplary Intracellular Base Solutions
  Ionic
    40–80 mM $Na^+$;
    50–90 mM $K^+$;
    0.01–0.1 mM $Ca^{++}$;
    5–25 mM $Mg^{++}$;
    20–40 mM $Cl^-$;
  pH Buffers
    1–5 mM $H_2PO_4$;
    3–7 mM $HCO_3$;
    25–50 mM HEPES;
  Impermeants
    25–50 mM Lactobionate;
    10 mM–1 M Sucrose;
    15–30 Mannitol;
    1–10 Glucose;
    50–100 Gluconate;
  Colloids
  6% Dextran 40;
  Pharmacologics
    0.1–2 mM Adenosine; and
    1–5 mM Glutathione.

High Potassium Exemplary Intracellular Base Solution
  Ionic
    62.5 mM $Na^+$;
    70.0 mM $K^+$;
    0.05 mM $Ca^{++}$;
    15.0 mM $Mg^{++}$;
    30.1 mM $Cl^-$;
  pH Buffers 2.5 mM $H_2PO_4$;
    5.0 mM $HCO_3$;
    35.0 mM HEPES;
  Impermeants
    30.0 mM Lactobionate;
    15.0 mM Sucrose;
    25.0 mM Mannitol;
    5.0 mM Glucose;
    70.0 mM Gluconate;
  Colloids 6% Dextran 40;
  Pharmacolopics
    2.0 mM Adenosine; and
    3.0 mM Glutathione.

This exemplary Intracellular Base Solution has an osmolality (mOsm/Kg) of 350, a pH of about 7.6, and a $[K^+][Cl^-]$ of about 2100.

Low Potassium Exemplary Intracellular Base Solutions
  Ionic
    100–150 mM $Na^+$;
    15–40 mM $K^+$;
    0.01–0.1 mM $Ca^{++}$;
    5–25 mM $Mg^{++}$;
    20–40 mM Cl;
  pH Buffers
    1–5 mM $H_2PO_4$;
    3–7 mM $HCO_3$;
    25–50 mM HEPES;
  Impermeants
    25–50 mM Lactobionate;
    10 mM–1M Sucrose;
    15–30 mM Mannitol;
    1–10 mM Glucose;
    50–100 mM Gluconate;
  Colloids 6% Dextran 40;
  Pharmacologics
    0.1–2 mM Adenosine; and
    1–5 mM Glutathione.

Exemplary Low Potassium Intracellular Solutions
  Ionic
    125 mM $Na^+$;
    25.0 mM $K^+$;
    0.05 mM $Ca^{++}$;
    15.0 mM $Mg^{++}$;
    30.1 mM $Cl^-$;
  pH Buffers
    2.5 mM $H_2PO_4$;

5.0 mM HCO$_3$;
35.0 mM HEPES;
Impermeants
30.0 mM Lactobionate;
15.0 mM Sucrose;
25.0 mM Mannitol;
5.0 mM Glucose;
70.0 mM Gluconate;
Colloids
6% Dextran 40;
Pharmacologics
2.0 mM Adenosine; and
3.0 mM Glutathione.
Exemplary Extracellular Base Solutions
Ionic
120–160 mM Na$^+$;
3–9 mM K$^+$;
1–3 mM Ca$^{++}$;
1–10 mM Mg$^{++}$;
100–150 mM Cl$^-$;
1–10 mM (SO$_4$)$^{2-}$;
pH Buffers
1–3 mM H$_2$PO$_4$;
20–30 mM HCO$_3$;
5–15 mM HEPES;
Impermeants
5–10 mM Glucose;
Colloids
6% Dextran 40;
Pharmacologics
0.1–2 mM Adenosine; and
1–5 mM Glutathione.
Exemplary Extracellular Base Solution
Ionic
141.2 mM Na$^+$;
6.0 mM K$^+$;
1.5 mM Ca$^{++}$;
5.0 mM Mg$^{++}$;
122.0 mM Cl$^-$;
1.0 mM SO$_4^-$;
pH Buffers
1.2 mM H$_2$PO$_4$;
25.0 mM HCO$_3$;
25.0 mM HEPES;
Impermeants
5.0 mM Glucose;
Colloids
6% Dextran 40;
Pharmacologics
1.0 mM Adenosine; and
3.0 mM Glutathione.

This exemplary extracellular base solution has an osmolality (mOsm/Kg) of 315, a pH of about 7.5, and a [K$^+$][Cl$^-$] of about 732.

EXAMPLES

Example 1

Hypothermic Preservation of Tissue Culture Cells

Preliminary experiments were undertaken to examine the viability of cells after hypothermic exposure in the high potassium exemplary embodiment of this invention and in other storage media at 4° C. These experiments were carried out using a canine kidney cell line (MDCK), since this provided a comparative reference with previous work in the development of hypothermic solutions. Cells were plated at 1×10$^4$ cells/well in Dulbecco's Modified Essential Medium (DMEM) for culture at 37° C. The next day, the plate was placed on ice and the DMEM media was replaced with 100 μl of one of the four storage solutions evaluated in this experiment, as specified in FIG. 1. Each plate was kept at 4° C. for either one or five days. After storage, the vehicle solution was removed and replaced with DMEM culture medium in preparation for the assessment of viability using Alamar Blue, which is a non-toxic indicator of mitochondrial oxidative phosphorylation and as such directly measures the metabolic status of cells.

It can be seen from the data summarized in FIG. 1 that, after 24 hours exposure at 4° C., the viability index for cells stored in Dulbecco's Modified Essential Medium (DMEM) was about as low as the "no-cell" baseline control, indicating that standard DMEM culture medium confers no protection during this period of hypothermic storage. The response of cells stored in EuroCollins (EC) was marginally better but significantly inferior compared with the indices for cells stored in the two "intracellular" solutions (the high potassium exemplary embodiment of this invention, and Viaspan™). We conclude that "intracellular" solutions, such as that of the invention and Viaspan™, offer superior cytoprotection during hypothermic exposure, compared with either standard culture media or EuroCollins organ preservation solution. Moreover, on the basis of this preliminary study, the new solution of this invention offers at least equivalent protection to other established hypothermic solutions, including the industry standard for organs, Viaspan™. These experiments have been expanded to include 24-hour storage of porcine kidneys, as described below.

These studies have been extended to include two additional cell types in vitro and examined cell viability using Alamar Blue at different time points following hypothermic storage. The vascular smooth muscle cell line (A10) and a bovine pulmonary endothelial cell line (CPAE) were used in these experiments. Cells were plated at a density of 1×10$^4$ cells/well in standard cell culture media. The next day, the plates were placed on ice and the media was replaced with 100 μl of the various storage solutions (see FIGS. 2–5).

The plates were stored in the refrigerator at 4° C. for either one or three days. Following storage, the plates were again placed on ice and the storage solutions were replaced with media for measurement of cell viability with Alarnar Blue. Viability was measured at two points, either immediately after exposure (FIGS. 2–5), or for six consecutive days after exposure at 4° C. (FIGS. 6 and 7).

Figure 4:
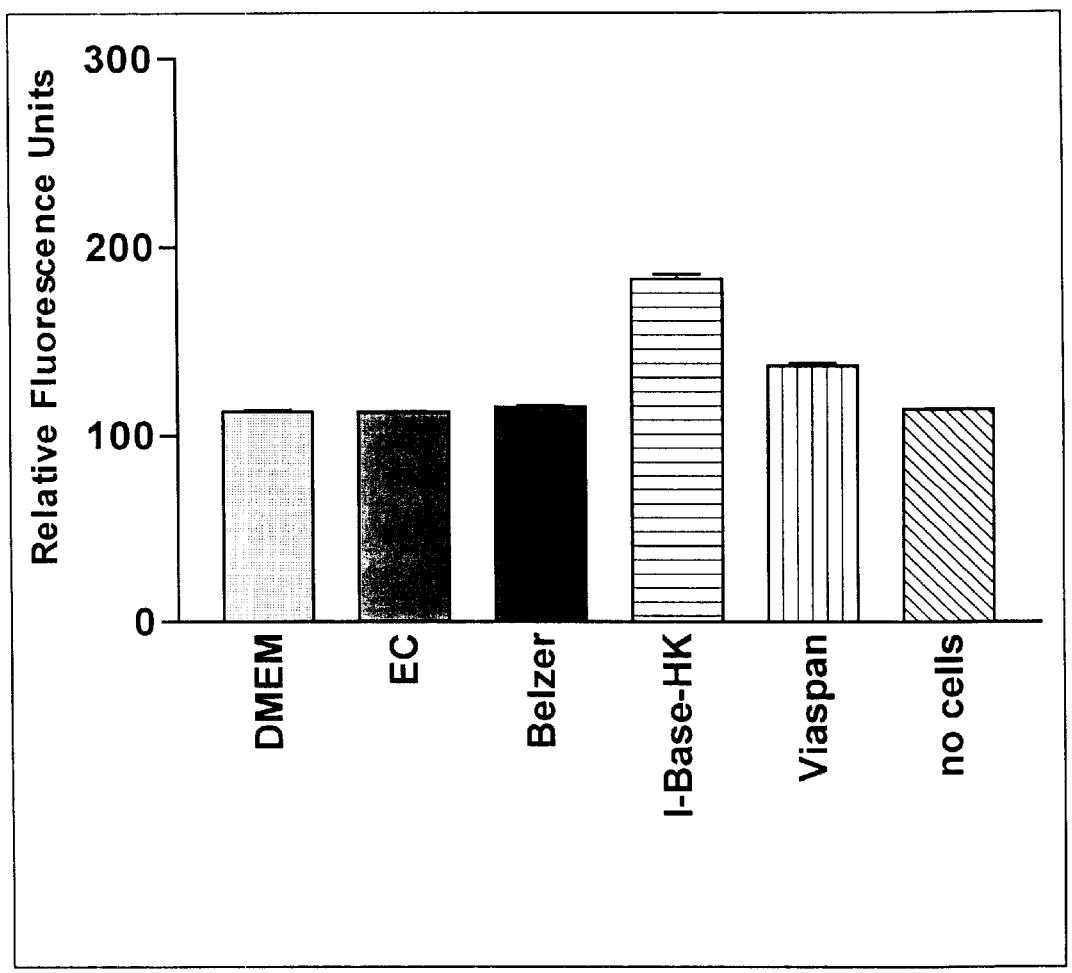
FIG. 4 shows the comparative viability of A10 cells after a 3-day storage interval.
Figure 5:
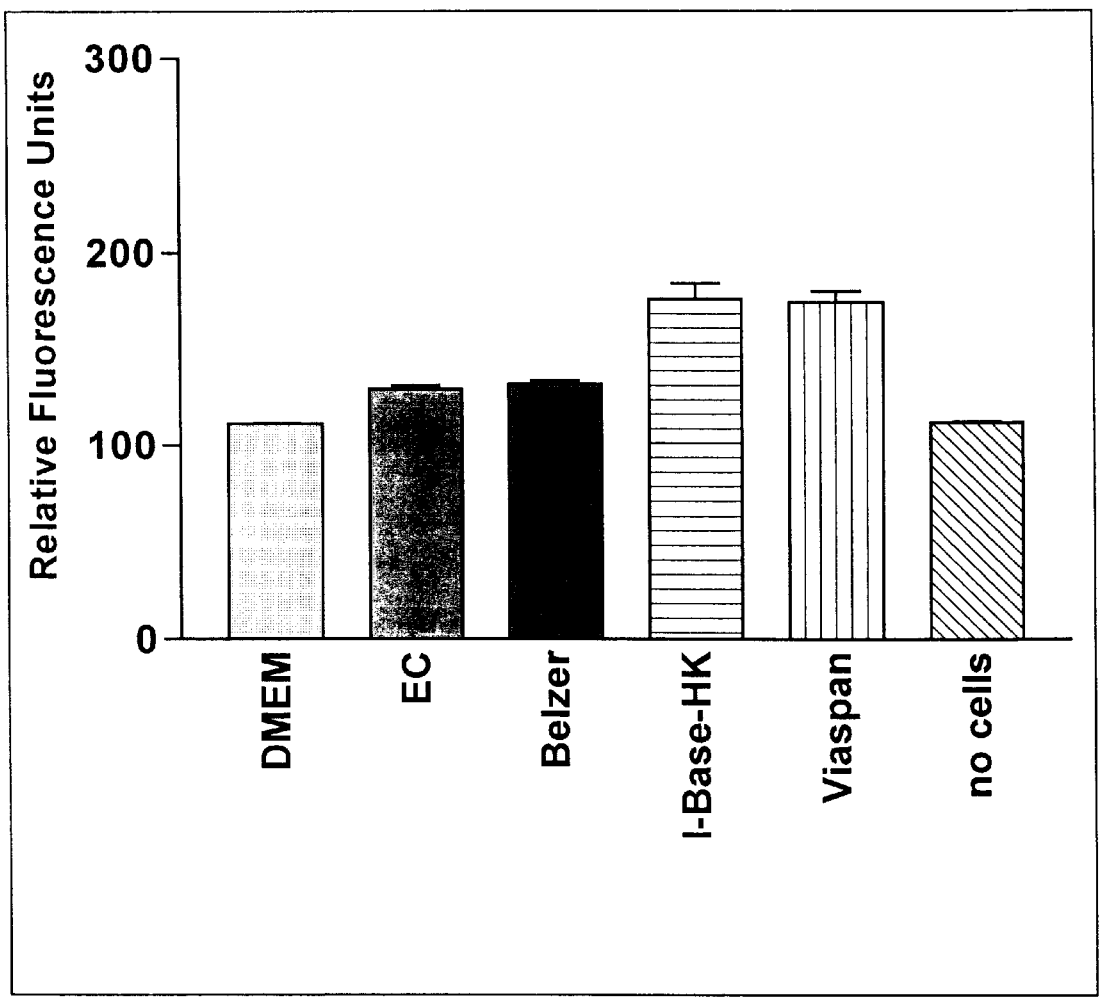
FIG. 5 shows the comparative viability of CPAE cells after a 3-day storage interval.

The comparative viability of cells at the end of each storage interval is shown in FIGS. 2–5. Viability of both cell types after 24 hours of hypothermic storage in UHK was equivalent or better than in Viaspan™ (FIGS. 2–5) After three days at 4° C., UHK demonstrated better viability than Viaspan™ for A10 cells, and similar viability for CPAE (FIGS. 4 and 5). By comparison, the other solutions, DMEM, EC and Belzer's MPS (Machine Perfusion Solution), all demonstrated inferior protection after three days of storage. Viability indices were no greater than background levels (no cells) for A10 cells at either one or three days hypothermic storage. In EC solution, CPAE cells demonstrated some viability after one day of hypothermic storage, but after three days, viability in EC was also down to background levels. DMEM and the Belzer solution were both at background levels after one and three days hypothermic storage for the CPAE cells.

Measurement of cell viability immediately after low temperature storage does not necessarily give a true indication of cell survival. Over time, cells may undergo further changes, including the repair of sub-lethal injury or cell death through the processes of apoptosis and necrosis. Whatever the eventual fate of hypothermically exposed cells may be, the processes required time for full manifestation and cell survival curves during the days following return to physiological temperatures are informative about the true state of viability. In light of these conditions, we further evaluated post-hypothermic viability during six consecutive days of culture at 37° C. (FIGS. 6 and 7). Such evaluation was possible because Alamar Blue is non-toxic to cells and can be used repeatedly on the same batch of cells as a non-destructive viability assay.

Figure 6:
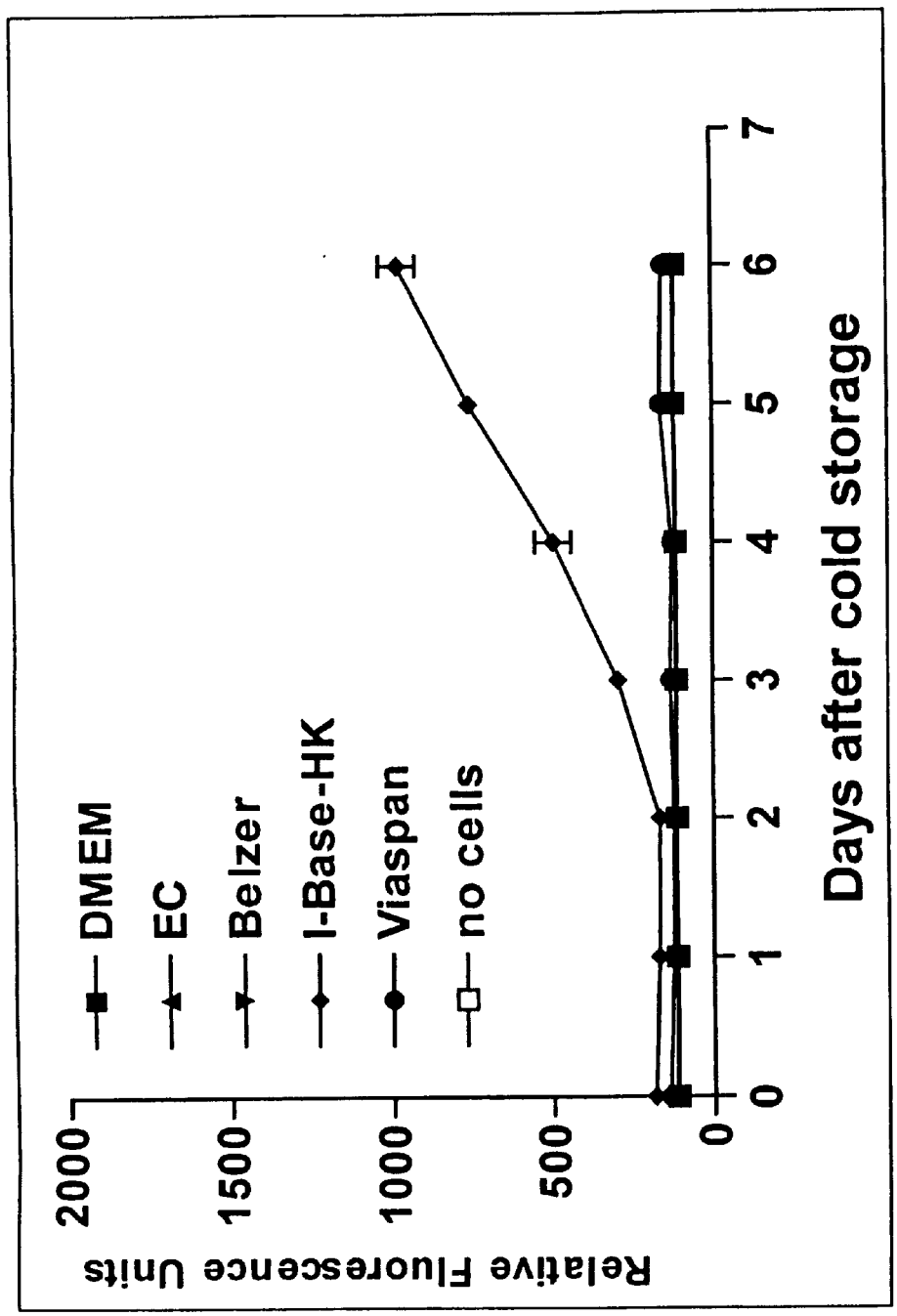
FIG. 6 shows the comparative viability of A10 cells during a 6 day period after a hypothermic storage interval of 3 days.
Figure 7:
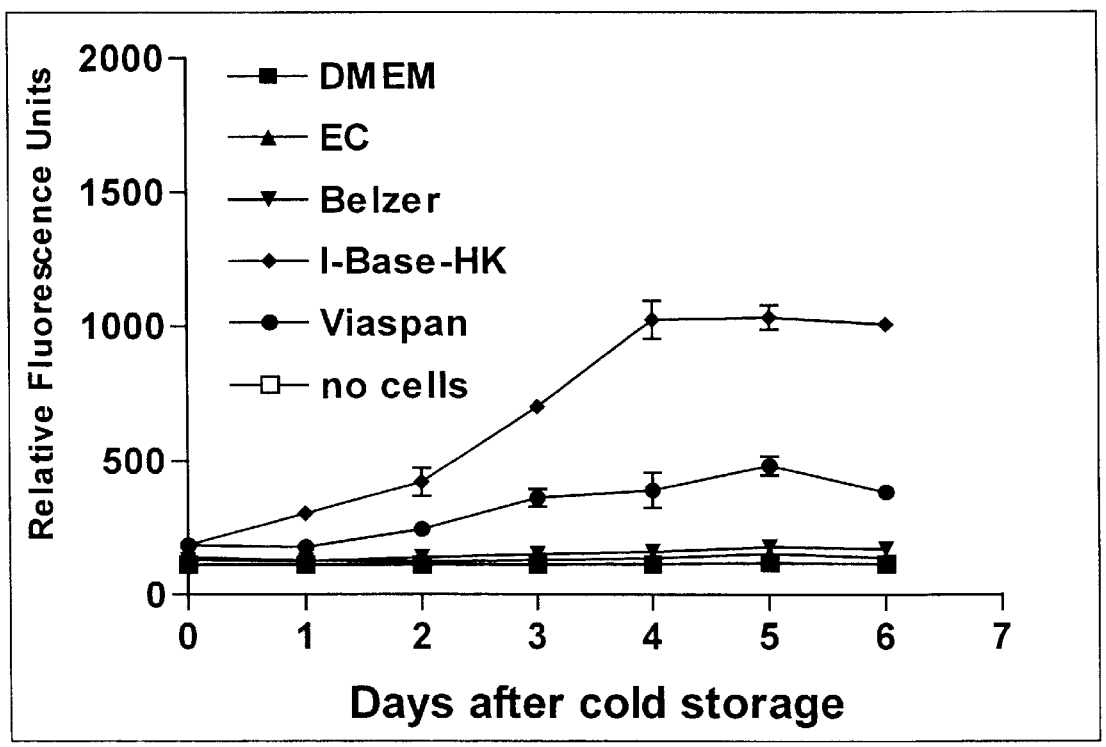
FIG. 7 shows the comparative viability of CPAE cells during a 6 day period after a hypothermic storage interval of 3 days.

FIGS. 6 and 7 illustrate that, in general, the high potassium example ("HK") provided equivalent, or better, preservation, than the other solutions. Both "intracellular" solutions, Viaspan™ and the high potassium example, proved to be superior compared with the other solutions. After three days of hypothermic storage, only CPAE cells stored in Viaspan™ or the high potassium example, and only the A10 cells kept in the high potassium example, were able to proliferate in culture.

These and similar observations indicate that the high potassium example is at least equal to, or superior to, other commonly used solutions employed for hypothermic storage of tissues and organs.

Example 2
Comparative Cryopreservation of Cells Using a Preferred Embodiment of the Exemplary High-K Intracellular-base Solution The same system as that described above for cells in microtiter plates was used to evaluate a preferred embodiment of the exemplary High-K Intracellular-base solution as a new carrier solution for cryoprotective additives (CPA). Specifically, a phosphate-free formulation of the new High-K solution was prepared to avoid the known precipitation of divalent cation phosphates in the presence of the cryoprotectant DMSO at low temperatures. Cell survival was compared after freezing and thawing in the presence of a range of concentrations of DMSO prepared in either the new phosphate-free HK-cryoprotectant vehicle solution (HK-CV), or EuroCollins medium. EuroCollins is an organ preservation solution that has also been used in the field of cryobiology as a vehicle solution for cryoprotectants.

Figure 15:
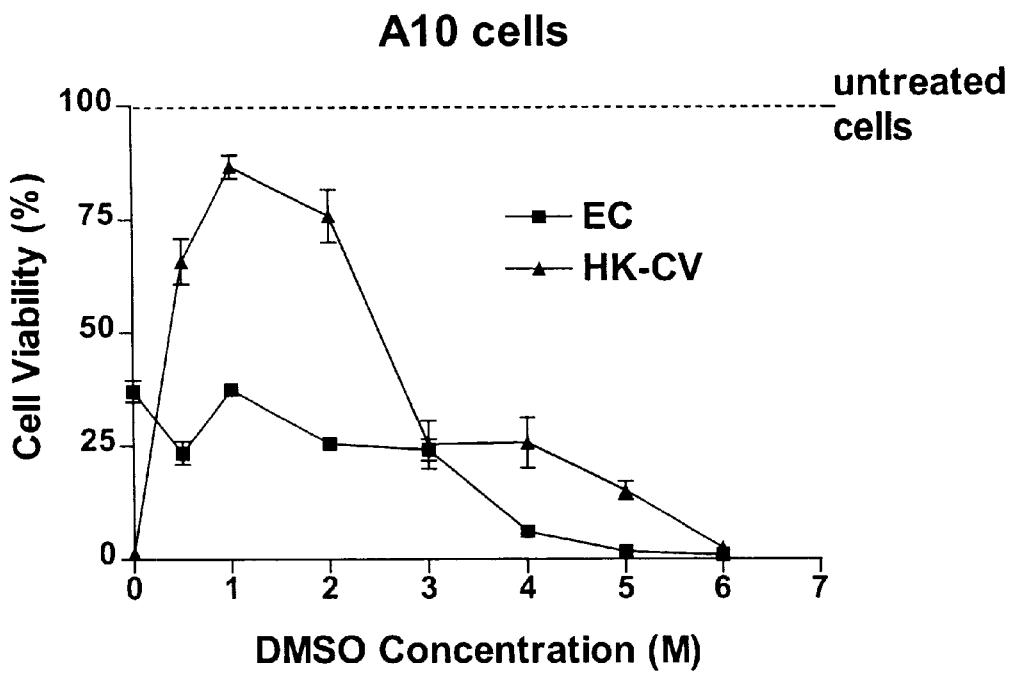
FIGS. 15 and 16 show comparative viability of cells cryopreserved with DMSO prepared in either the new phosphate-free, high potassium intracellular base vehicle solution (HK-CV), or EuroCollins solution. Data represents the mean (±SEM) of 4 replicate batches of cells.
Figure 16:
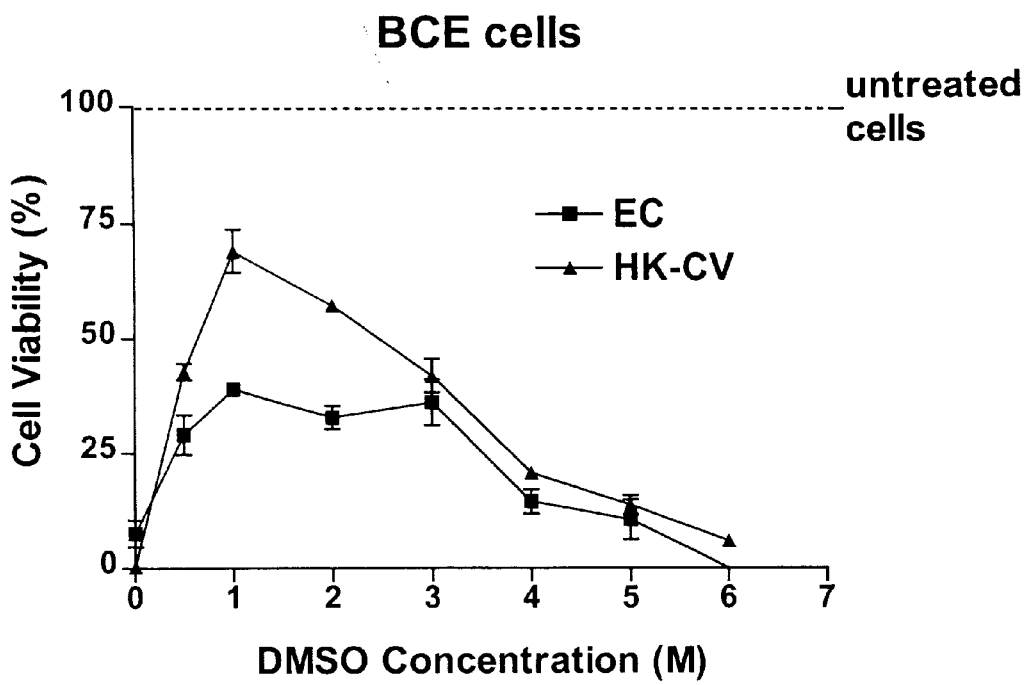

Cells were plated at $2 \times 10^4$ cells/well and after overnight incubation regular culture medium was replaced with the experimental CPA mixtures using the following protocol: Plates were cooled to –80° C. at a controlled rate (1° C./min) and stored overnight at –135° C. The plates were thawed using a two-step warming protocol and the CPA was diluted using mannitol as an osmotic buffer. Cell viability was assessed using the Alamar Blue assay of cellular metabolic activity at 37° C. FIGS. 15 and 16 show the comparative viability of two cell types after cryopreservation in the respective media. The data show that optimum survival of both types of cells was achieved using 1–2 molar DMSO, but the percentage viability, normalized to untreated cells, was markedly higher for cells preserved in the new HK intracellular base vehicle solution compared with the Euro-Collins medium. This was consistent for both the A10 smooth muscle cells and the bovine corneal endothelial (BCE) cells.

Example 3
Structural Integrity of Hypothermically Stored Veins

Hypothermic storage of whole organs flushed or perfused with a preservation solution is common practice in clinical transplantation. This procedure leaves the vascular endothelial cells in direct contact with the preservation medium during the cold ischemic period. The effect of storage conditions on the integrity of vascular endothelium is therefore of crucial importance for the quality of preservation of intact organs.

A pilot study was conducted to compare microscopic changes in tissue morphology when harvested vessels were immersed and transported in the high potassium example hypothermic preservation solution compared with the Dulbecco's Minimum Essential Medium (DMEM) which is a common culture medium used to incubate and transport tissues ex vivo. For three separate experiments, fresh jugular veins were harvested from rabbits (by the method we have used extensively) and immersed in either pre-cooled DMEM or the high potassium example. Both solutions were kept on ice. Tissue samples were then transported to the laboratory where the vessels were cut into segments for fixation and processing for histopathology. The total cold ischemia time in these experiments was relatively short, 34.5±9.5 minutes for samples transported in DMEM, and 37±4 minutes for samples in the high potassium example.

Figure 8:
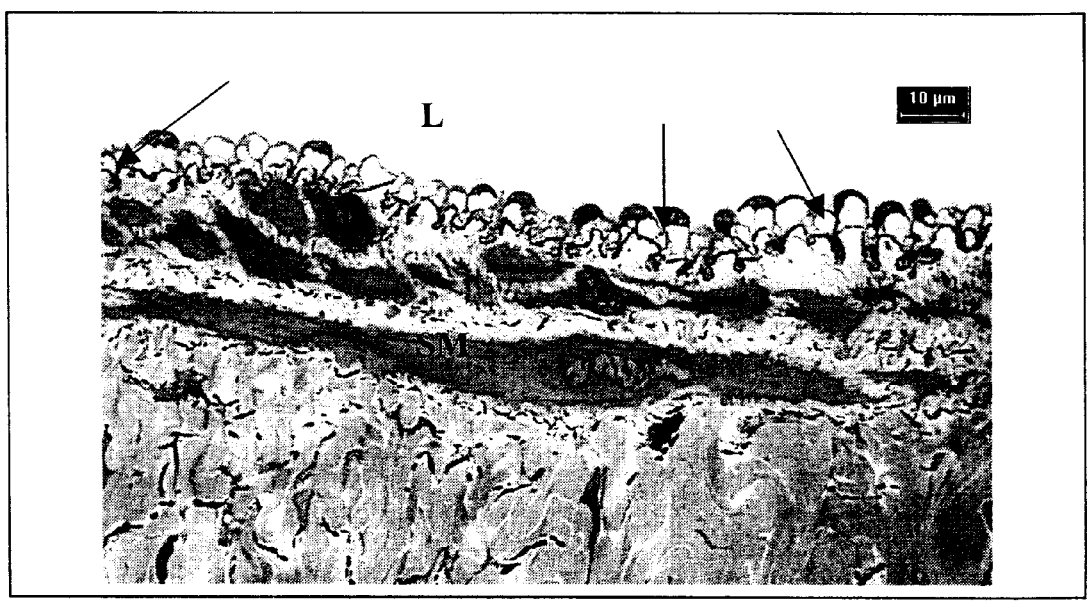
FIG. 8 shows light microscopy histology of jugular vein segments after a period of cold ischemia in DMEM culture medium.

Tissue immersed and transported in DMEM on ice exhibited microscopic changes within the tunica intima and tunica media, as shown in FIG. 8. The intima was intact, but there was extreme vacuolization (indicated by the arrows) of the underlying basal lamina causing, in turn, extrusion of the endothelial cells into the lumen and giving a "rounding-up" appearance. Apart from this vacuolization, the endothelial cells had a near normal appearance. The smooth muscle cells (SM) had a somewhat shrunken appearance with irregular contours. The tunica adventitia was essentially normal. The lumen L is also shown.

Figure 9:
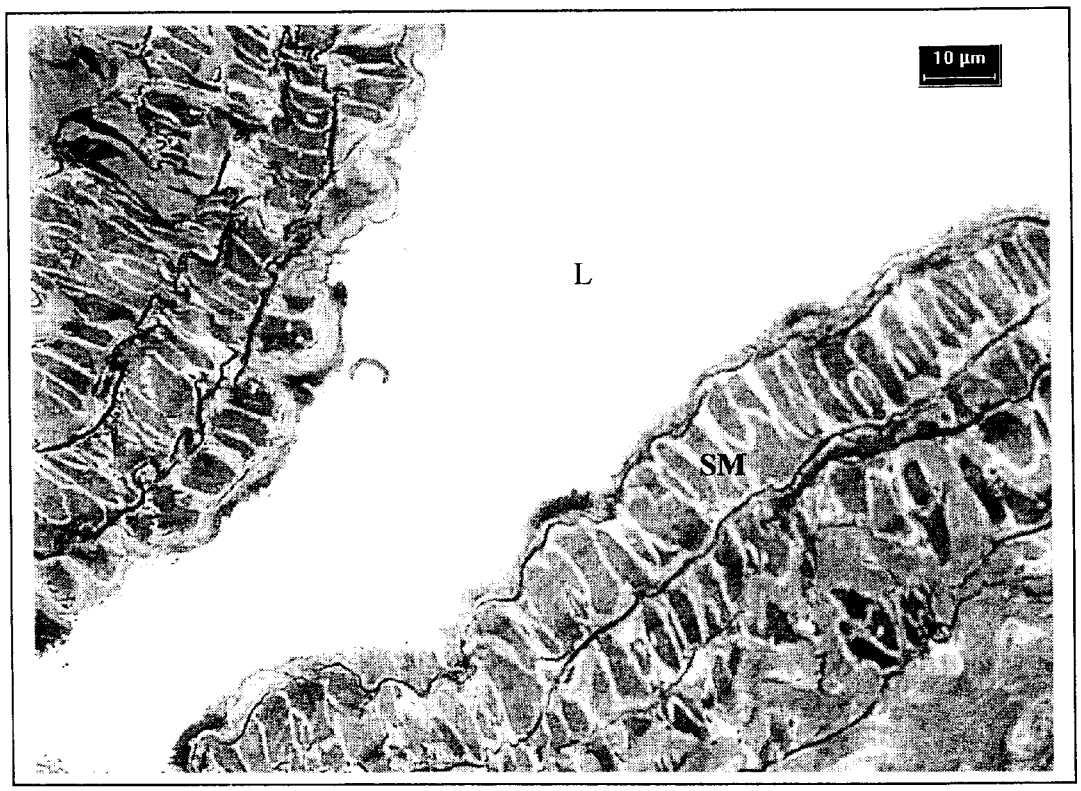
FIG. 9 shows light microscopy histology of jugular vein segments after a period of cold ischemia in "I-Base-HK" preservation solution in accordance with this invention.

In contrast, jugular veins transported in the high potassium example demonstrated little if any histological changes compared with the DMEM group as shown in FIG. 9. The tunica intima was intact with little evidence of vacuolization of the underlying basement membrane. The smooth muscle cells (SM) did not appear shrunken and were in a normal, horizontal orientation.

These preliminary experiments demonstrate that in veins stored in culture medium, cold ischemia results in microscopic changes within less than one hour. In contrast, the high potassium example-stored veins did not demonstrate these microscopic changes. These are important observations since, historically, it has been concluded that saline is not the best preservation fluid even for short-term storage. Moreover, several studies have demonstrated how sensitive the endothelial layer is to handling. For example, it has been shown that cold preservation resulted in severe endothelial cell changes and significant detachment after only 3 hours of cold storage. Many other studies, however, have documented morphologic and functional damage to endothelial cells induced by cold storage in autologous whole blood, normal saline solution, and Ringer's lactate. A recent study compared the "Gold Standard" organ preservation solution, Viaspan™, with autologuous whole blood and normal saline solution for canine vein storage. The study demonstrated that post-implantation intimal hyperplasia and vascular physiology were similar in Viaspan™-treated vein grafts and fresh, untreated controls. In contrast, both the other treatment groups demonstrated statistically significant changes. Nevertheless, others have reported that hyperkalemic-type solutions (of which Viaspan™ is an example) can cause thrombophlebitis and decreased fibrinolytic activity of venous endothelium. As discussed above, there were documented concerns for the detrimental effects on the heart of very high potassium levels (>100 mM) found in many organ preservation solutions.

Example 4
Comparative Organ Preservation Studies using the High Potassium Example A. Comparison of new High-K (HK) solution with Belzer Machine Perfusion Solution A new intracellular-base high potassium solution was compared with an established solution (Belzer machine perfusion solution [MPS]) during continuous 18–20 hour perfusion preservation of canine kidneys procured after one hour of warm ischemia. Following procurement from adult mongrel dogs (n=5), both kidneys were flushed with Viaspan solution and stored at 4° C. for approximately two hours prior to initiation of perfusion. Perfusion was performed using a multiple organ recovery perfusion prototype with two independent circuits. One kidney was perfused with the new intracellular-base high potassium solution and the contralateral kidney with Belzer MPS, both at ~9° C. and a controlled pressure of 35–40 mmHg. After 18–20 hours of perfusion, the kidneys were transplanted ectopically using a canine carotid artery model.

Figure 10:
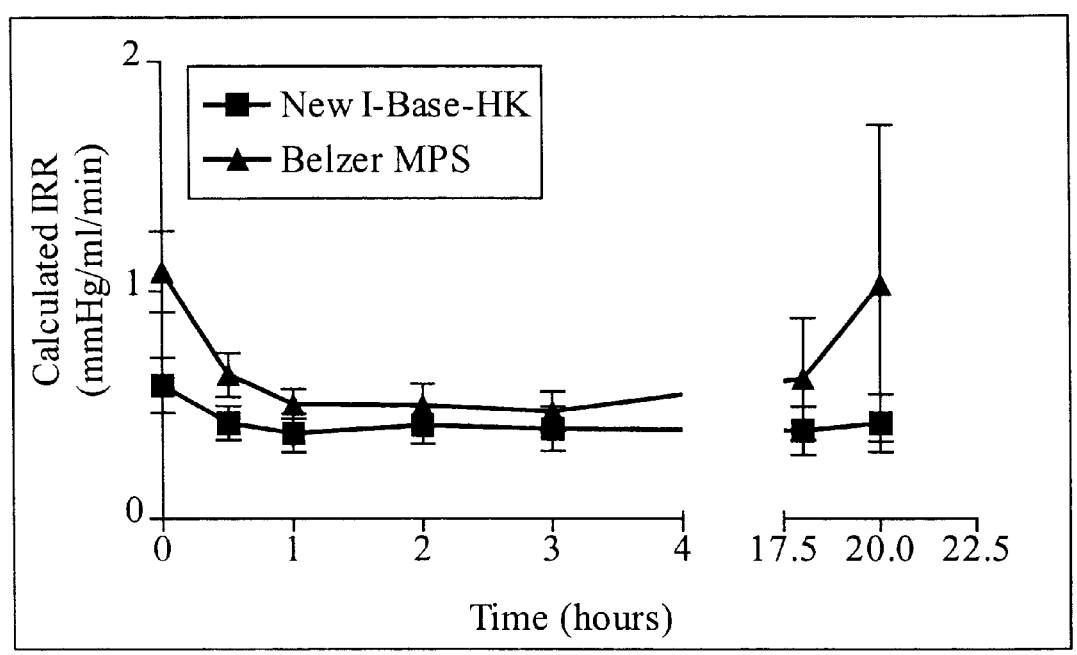
FIG. 10 shows internal renal resistance measurements for canine kidneys perfused at ~9° C.
Figure 11:
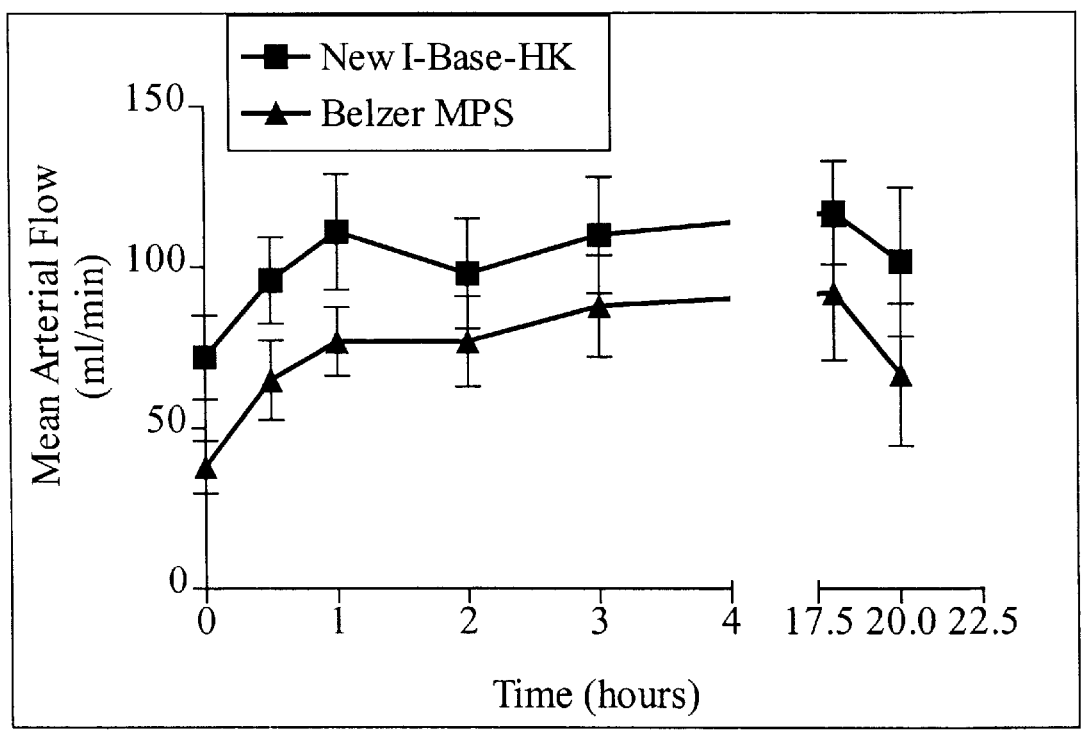
FIG. 11 shows arterial flow rates for canine kidneys perfused at 9° C.
Figure 12:
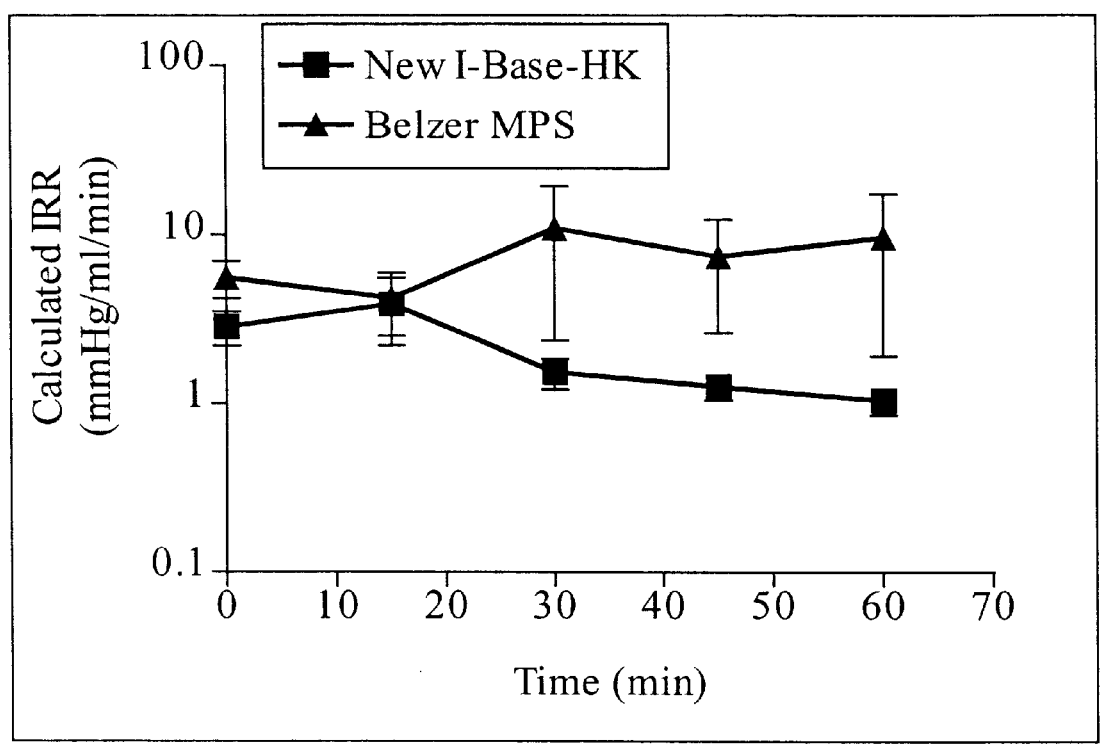
FIG. 12 shows internal renal resistance measured in vivo for preserved kidneys transplanted ectopically after 20 hours machine perfusion preservation.
Figure 13:
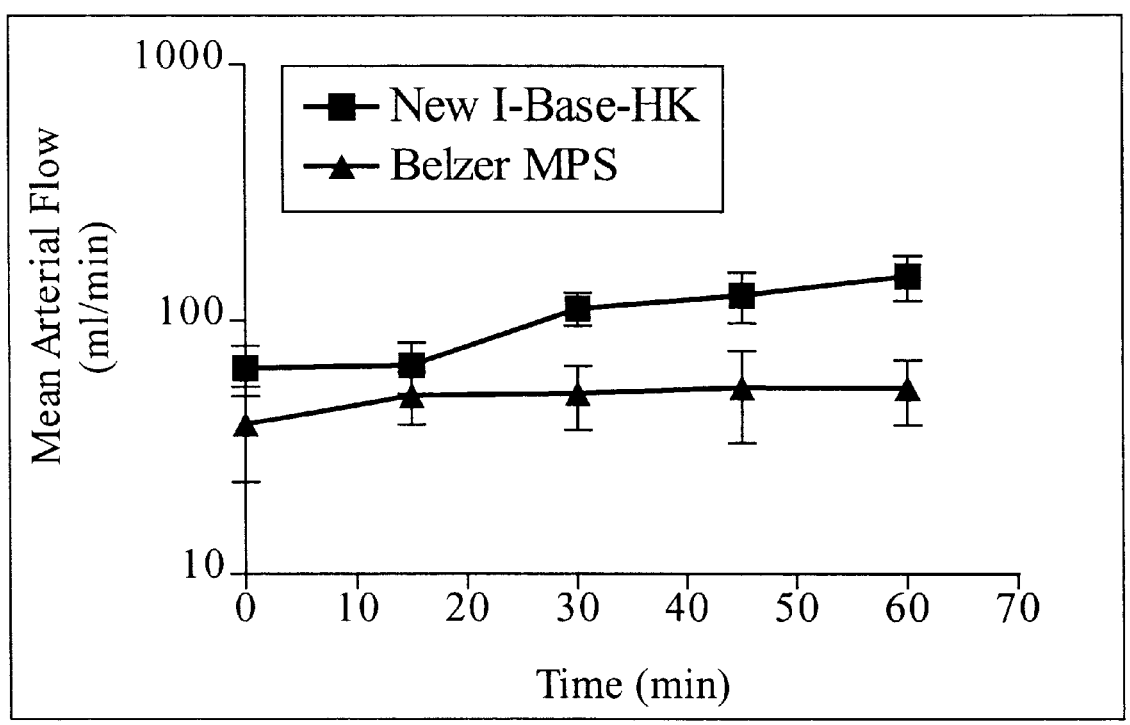
FIG. 13 shows mean arterial flow measured in vivo for preserved kidneys transplanted ectopically after 20 hours machine perfusion preservation.

FIGS. 10 and 11, which show that mean arterial flow was higher at each time point for kidneys perfused with the new solution compared with MPS and the vascular resistance curve was lower for the new solution group of kidneys. In general, these physiological parameters were similar in both groups during in vitro perfusion. At the end of one hour in vivo, however, the new solution-perfused kidneys exhibited higher arterial flow rates (p<0.05) and lower internal renal resistances (p<0.05) than the kidneys perfused with Belzer MPS (FIG. 6).

The results suggest that the new solution may be a superior alternative to Belzer MPS for perfusion preservation of kidneys.

B. Comparison of new High K solution with Viaspan solution in a swine model

Figure 14:
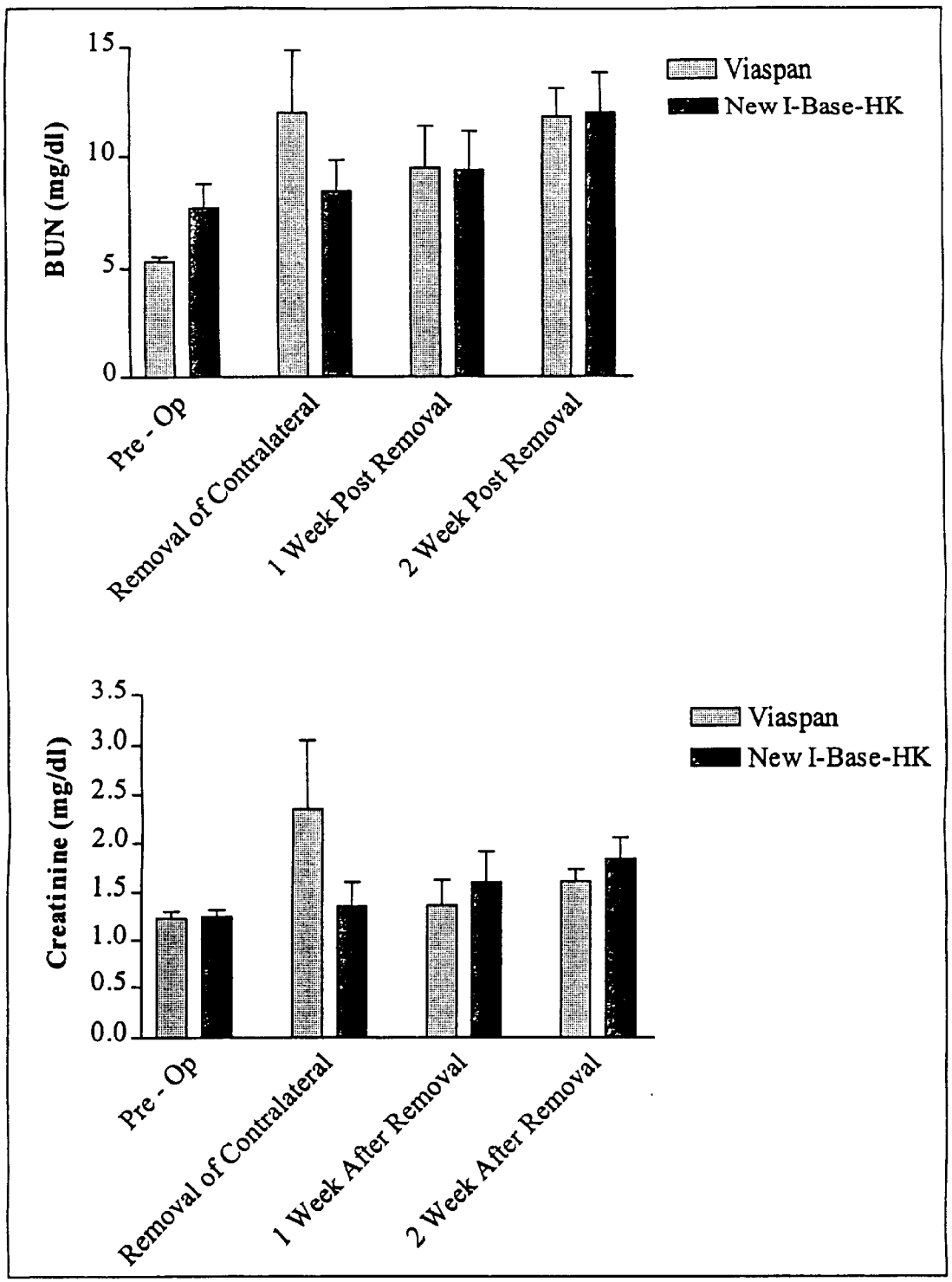
FIG. 14 shows biochemical indicators (creatinine and BUN) of kidney function for pig kidneys transplanted after a minimum of 20 hour cold storage preservation.

The efficacy of a new intracellular-base high potassium solution, which fulfills the minimum theoretical requirements for organ cold storage, was compared with commercial Viaspan in an established pig kidney transplant model. These in vivo studies were performed using an autologous swine model in which a kidney was removed, flushed and stored with either the new high potassium solution (n=5) or Viaspan (n=5) for at least 20 hours prior to reimplantation. The contralateral unoperated kidney was removed 5–7 days later and the performance of the preserved kidney determined by assessments of BUN, creatinine and histopathology. FIG. 14, presents Biochemical indicators (Creatinine and BUN) of kidney function for pig kidneys transplanted after a minimum of 20 hours cold storage preservation in either new intracellular-base high potassium solution, or Viaspan, shows that no statistically significant differences was observed between the two groups of all assessment criteria. In conclusion, these pre-clinical results indicate that the base formulation of the new high potassium solution provides hypothermic kidney cell preservation that is at least equivalent to that of the established standard, Viaspan, during clinically relevant periods of kidney storage.

What is claimed is:

1. An organ and/or tissue procurement, preservation, transplantation and/or bloodless surgery solution, comprising:

40–80 mM $Na^+$;
50–90 mM $K^+$;
0.01–0.1 mM $Ca^{++}$
5–25 mM $Mg^{++}$;
20–40 mM $Cl^-$;
1–5 mM $H_2PO_4$;
3–7 mM $HCO_3$;
25–50 mM HEPES;
25–50 mM Lactobionate;
10 mM- 1 M Sucrose;
15–30 mM Mannitol;
1–10 mM Glucose;
50–100 mM Gluconate;
about 6% Dextran 40;
0.1–2 mM Adenosine; and optionally
1–5 mM Glutathione.

2. The solution of claim 1, wherein said solution further comprises 1–5 mM Glutathione.

3. The solution of claim 1, comprising:

about 62.5 mM $Na^+$;
about 70.0 mM $K^+$;
about 0.05 mM $Ca^{++}$;
about 15.0 mM $Mg^{++}$;
about 30.1 mM $Cl^-$;
about 2.5 mM $H_2PO_4$;
about 5.0 mM $HCO_3$;
about 35.0 mM HEPES;
about 30.0 mM Lactobionate;
about 15.0 mM Sucrose;
about 25.0 mM Mannitol;
about 5.0 mM Glucose;
about 70.0 mM Gluconate;
about 6% Dextran 40; and
about 2.0 mM Adenosine.

4. The solution of claim 3, wherein said solution further comprises about 3.0 mM Glutathione.

5. The solution pf claim 1, wherein said solution has an osmolality (mOsm/Kg) of about 350, a pH of about 7.6, and a $[K^+][Cl^-]$ of about 2100.

6. An organ and/or tissue procurement, preservation, transplantation and/or bloodless surgery solution, comprising:

120–160 mM $Na^+$;
3–9 mM $K^+$;
1–3 mM $Ca^{++}$;
1–10 mM $Mg^{++}$;
122–150 mM $Cl^-$;
1–10 mM $(SO_4)^{2-}$;
1–3 mM $H_2PO_4$;
20–30 mM $HCO_3$;
5–15 mM HEPES;
5–10 mM Glucose;
about 6% Dextran 40;
0.1–2 mM Adenosine; and optionally
1–5 mM Glutathione.

7. The solution of claim 6, wherein said solution further comprises 1–5 mM Glutathione.

8. An organ and/or tissue procurement, preservation, transplantation and/or bloodless surgery solution, comprising:

about 141.2 mM $Na^+$;
about 6.0 mM $K^+$;

about 1.5 mM Ca$^{++}$;
about 5.0 mM Mg$^{++}$;
about 122.0 mM Cl$^-$;
about 1.0 mM (SO$_4$)$^{2-}$;
about 1.2 mM H$_2$PO$_4$;
about 25.0 mM HCO$_3$;
about 25.0 mM HEPES;
about 5.0 mM Glucose;
about 6% mM Dextran 40; and
about 1.0 mM Adensine.

9. The solution of claim 8, wherein said solution further comprises about 3.0 mM Glutathione.

10. The solution of claim 8, wherein said solution has an osmolality (mOsm/Kg) of about 315, a pH of about 7.5, and a [K$^+$][Cl$^-$] of about 732.

11. A solution kit, comprising a saleable package containing:
1) at least one first container containing at least one base electrolyte solution, wherein the solution comprises
40–80 mM Na$^+$;
50–90 mM K$^+$;
Ca$^{++}$;
Mg$^{++}$;
Cl$^-$;
H$_2$PO$_4^-$;
HCO$_3^-$;
HEPES;
Lactobionate;
Sucrose;
Mannitol;
Glucose;
Gluconate;
Dextran 40; and
Adenosine; and
2) at least two second containers respectively containing different additives for converting said base solution to different mixed solutions for use in different stages of procurement, preservation or transplantation of an organ or tissue.

12. The kit of claim 11, wherein said at least one first container comprises at least one container containing an intracellular base solution, and at least one container containing an extracellular base solution.

13. The kit of claim 11, wherein at least one said additive is a purge additive for purging an organ or tissue of blood.

14. The kit of claim 11, wherein at least one said additive is a cryoprotection additive.

15. The kit of claim 14, wherein the base solution is an intracellular base solution.

16. The kit of claim 11, wherein at least one said additive is a rescue additive.

17. The kit of claim 16, wherein the base solution is an extracellular base solution.

18. The kit of claim 11, wherein at least one said additive is a rinse additive for flushing unwanted preservation molecules away from an organ or tissue.

19. The kit of claim 18, wherein the base solution is an extracellular base solution.

20. The kit of claim 11, wherein said base solution further comprises Glutathione or wherein said kit further comprises a container containing Glutathione.

21. The kit of claim 11, wherein said base solution comprises:
40–80 mM Na$^+$;
50–90 mM K$^+$;
0.01–0.1 mM Ca$^{++}$;
5–25 mM Mg$^{++}$;
20–40 mM Cl$^-$;
1–5 mM H$_2$PO$_4$;
3–7 mM HCO$_3$;
25–50 mM HEPES;
25–50 mM Lactobionate;
10 mM– 1 M Sucrose;
15–30 mM Mannitol;
1–10 mM Glucose;
50–100 mM Gluconate;
about 6% Dextran 40;
0.1–2 mM Adenosine; and optionally
1–5 mM Glutathione.

22. The kit of claim 21, wherein said base solution futrther comprises 1–5 mM Glutathione or wherein said kit further comprises a container containing an amount of Glutathione that, when added to the base solution, produces a base solution that comprises 1–5 mM Glutathione.

23. The kit of claim 21, wherein said base solution has an osmolality (mOsm/Kg) of about 350, a pH of about 7.6, and a [K$^+$][Cl$^-$] of about 2100.

24. The kit of claim 11, wherein said base solution comprises:
about 62.5 mM Na$^+$;
about 70.0 mM K$^+$;
about 0.05 mM Ca$^{++}$;
about 15.0 mM Mg;
about 30.1 mM Cl$^-$;
about 2.5 mM H$_2$PO$_4$;
about 5.0 mM HCO$_3$;
about 35.0 mM HEPES;
about 30.0 mM Lactobionate;
about 15.0 mM Sucrose;
about 25.0 mM Mannitol;
about 5.0 mM Glucose;
about 70.0 mM Gluconate;
about 6% Dextran 40; and
about 2.0 mM Adenosine.

25. The kit of claim 24, wherein said base solution further comprises about 3.0 mM Glutathione or wherein said kit further comprises a container containing an amount of Glutathione that, when added to the base solution, produces a base solution that comprises about 3.0 mM Glutathione.

26. A solution kit, comprising a saleable. package containing:
1) at least one first container containing at least one base electrolyte solution, wherein the solution comprises:
120–160 mM Na$^+$;
3–9 mM K$^+$;
1–3 mM Ca$^{++}$;
1–10 mM Mg$^{++}$;
122–150 mM Cl$^-$;
1–10 mM (SO$_4$)$^{2-}$;
1–3 mM H$_2$PO$^4$;
20–30 mM HCO$_3$;
5–15 mM HEPES;
5–10 mM Glucose;
6% Dextran 40; and
0.1–2 mM Adenosine; and
2) at least two second containers respectively containing different additives for converting said base solution to different mixed solutions for use in different stages of procurement, preservation or transplantation of an organ or tissue.

27. The kit of claim 26, wherein said base solution further comprises Glutathione or wherein said kit further comprises a container containing Glutathione.

28. The kit of claim 26, wherein said base solution further comprises 1–5 mM Glutathione or wherein said kit further comprises a container containing an amount of Glutathione that, when added to the base solution, produces a base solution that comprises 1–5 mM Glutathione.

29. The kit of claim 28, wherein said base solution comprises about 3.0 mM Glutathione or wherein said kit comprises a container containing an amount of Glutathione that, when added to the base solution, produces a base solution that comprises about 3.0 mM Glutathione.

30. The kit of claim 26, wherein said base solution has an osmolality (mOsm/Kg) of about 315, a pH of about 7.5, and a $[K^+][Cl^-]$ of about 732.

* * * * *